(12) United States Patent
Tamura et al.

(10) Patent No.: US 9,375,365 B2
(45) Date of Patent: Jun. 28, 2016

(54) ABSORBENT ARTICLE

(71) Applicant: UNICHARM CORPORATION, Shikokuchuo-shi, Ehime (JP)

(72) Inventors: Tatsuya Tamura, Kanonji (JP); Yuki Noda, Kanonji (JP); Takashi Nomoto, Kanonji (JP); Takashi Onozuka, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/381,928

(22) PCT Filed: Dec. 11, 2012

(86) PCT No.: PCT/JP2012/082087
§ 371 (c)(1),
(2) Date: Aug. 28, 2014

(87) PCT Pub. No.: WO2013/128755
PCT Pub. Date: Sep. 6, 2013

(65) Prior Publication Data
US 2015/0065984 A1    Mar. 5, 2015

(30) Foreign Application Priority Data

Feb. 29, 2012  (JP) ................................. 2012-044439

(51) Int. Cl.
*A61F 13/15* (2006.01)
*A61F 13/511* (2006.01)
(Continued)

(52) U.S. Cl.
CPC ....... *A61F 13/51104* (2013.01); *A61F 13/4756* (2013.01); *A61F 13/513* (2013.01); *A61L 15/20* (2013.01); *A61F 2013/51186* (2013.01); *A61F 2013/51355* (2013.01)

(58) Field of Classification Search
CPC ........... A61F 13/4756; A61F 13/51104; A61F 13/51108; A61F 13/51113; A61F 13/51117; A61F 13/5116; A61F 13/51165; A61F 13/51169; A61F 13/51173; A61F 13/51178; A61F 13/51182; A61F 13/51186; A61F 13/512; A61F 13/5121; A61F 13/5122; A61F 13/5123; A61F 13/5125; A61F 13/5126; A61F 13/515; A61F 13/51078; A61F 13/5108; A61F 13/51085
See application file for complete search history.

(56) References Cited

U.S. PATENT DOCUMENTS 3,929,135 A   12/1975   Thompson
4,588,630 A    5/1986   Shimalla
(Continued)

FOREIGN PATENT DOCUMENTS

CN    1432352        7/2003
EP    1250940 A1    10/2002
(Continued)

OTHER PUBLICATIONS

Atsushi Fujita, "Prediction of Organic Compounds and Organic Conceptual Diagram", Kagaku no Ryoiki (Region of Chemistry), Oct. 1957, p. 719-725, vol. 11, No. 10.
(Continued)

*Primary Examiner* — Bradley Philips
(74) *Attorney, Agent, or Firm* — Hauptman Ham, LLP

(57) ABSTRACT

Provided is an absorbent article capable of suppressing leakage in the widthwise direction from an absorbent article (1) of a bodily fluid (31) which has seeped from an absorbent body (4) as a result of the application of pressure to the absorbent article (1). The present invention is an absorbent article (1) having a lengthwise direction (Y-direction) and a widthwise direction (X-direction), and provided with a liquid-permeable top sheet (2) provided on the skin-side, a liquid-impermeable backsheet (3) provided on the garment-side, and a liquid-holding absorbent body (4) provided between the top sheet (2) and the backsheet (3) and including edges extending in the lengthwise direction on both sides in the widthwise direction, wherein: at least areas outside both edges of the absorbent body (4) in the widthwise direction thereof include a plurality of first channels (21) and a plurality of second channels (22) for channeling bodily fluid (31) which has seeped from the absorbent article (4); the plurality of first channels (21) extend in the lengthwise direction and are arranged in the widthwise direction; and the plurality of second channels (22) connect adjacent first channels (21).

11 Claims, 15 Drawing Sheets

(51) Int. Cl.
  *A61F 13/475* (2006.01)
  *A61F 13/513* (2006.01)
  *A61L 15/20* (2006.01)

(56) References Cited

U.S. PATENT DOCUMENTS

| | | | |
|---|---|---|---|
| 4,759,754 A | 7/1988 | Korpman | |
| 5,078,710 A | 1/1992 | Suda et al. | |
| 5,181,563 A * | 1/1993 | Amaral | A61F 13/4752 604/378 |
| 5,334,176 A | 8/1994 | Buenger et al. | |
| 5,344,416 A | 9/1994 | Niihara | |
| 5,614,283 A | 3/1997 | Potnis et al. | |
| 5,650,214 A | 7/1997 | Anderson et al. | |
| 6,153,209 A | 11/2000 | Vega et al. | |
| 6,277,104 B1 * | 8/2001 | Lasko | A61F 13/512 604/368 |
| 6,503,598 B1 * | 1/2003 | Goda | A61F 13/512 428/131 |
| 6,730,819 B1 | 5/2004 | Pesce | |
| 2001/0029141 A1 | 10/2001 | Mizutani et al. | |
| 2003/0088222 A1 | 5/2003 | Yoshimasa et al. | |
| 2003/0149410 A1 | 8/2003 | Kudo et al. | |
| 2003/0198784 A1 | 10/2003 | Mizutani et al. | |
| 2006/0184150 A1 | 8/2006 | Noel | |
| 2006/0276767 A1 | 12/2006 | Ueminami et al. | |
| 2007/0219515 A1 | 9/2007 | Marsh et al. | |
| 2007/0298213 A1 | 12/2007 | Noda et al. | |
| 2007/0298214 A1 | 12/2007 | Noda et al. | |
| 2007/0298220 A1 | 12/2007 | Noda et al. | |
| 2007/0298667 A1 | 12/2007 | Noda et al. | |
| 2007/0298671 A1 | 12/2007 | Noda et al. | |
| 2007/0299416 A1 | 12/2007 | Noda et al. | |
| 2008/0010795 A1 | 1/2008 | Mizutani et al. | |
| 2008/0044622 A1 | 2/2008 | Noda et al. | |
| 2008/0044628 A1 | 2/2008 | Noda et al. | |
| 2008/0045915 A1 | 2/2008 | Noda et al. | |
| 2008/0085399 A1 | 4/2008 | Noda et al. | |
| 2008/0132136 A1 | 6/2008 | Uematsu et al. | |
| 2008/0200894 A1 | 8/2008 | Gatto et al. | |
| 2009/0221978 A1 | 9/2009 | Gatto et al. | |
| 2009/0282660 A1 | 11/2009 | Noda et al. | |
| 2010/0069874 A1 | 3/2010 | Noda et al. | |
| 2010/0137824 A1 | 6/2010 | Uematsu et al. | |
| 2010/0179494 A1 * | 7/2010 | Kuroda | A61F 13/15739 604/365 |
| 2010/0191207 A1 | 7/2010 | Oba et al. | |
| 2011/0319851 A1 | 12/2011 | Kudo et al. | |
| 2012/0045620 A1 | 2/2012 | Oba et al. | |
| 2012/0123365 A1 * | 5/2012 | Pan | A61K 8/0208 604/367 |
| 2012/0141742 A1 | 6/2012 | Yamaguchi et al. | |
| 2012/0177889 A1 | 7/2012 | Uematsu et al. | |
| 2012/0196091 A1 | 8/2012 | Mizutani et al. | |
| 2013/0034686 A1 | 2/2013 | Mitsuno | |
| 2013/0137328 A1 | 5/2013 | Mitsuno | |
| 2013/0226123 A1 | 8/2013 | Kudo et al. | |

FOREIGN PATENT DOCUMENTS

| | | |
|---|---|---|
| EP | 1362568 | 11/2003 |
| EP | 1371379 A1 | 12/2003 |
| EP | 1990033 A1 | 11/2008 |
| EP | 2011463 A2 | 1/2009 |
| EP | 2036521 | 3/2009 |
| EP | 2433602 | 3/2012 |
| GB | 2262235 A | 6/1993 |
| JP | S57-17081 | 4/1982 |
| JP | S64-34365 | 2/1989 |
| JP | S64-56051 A | 3/1989 |
| JP | H01-158954 | 6/1989 |
| JP | H02-152920 | 6/1990 |
| JP | H02-229255 | 9/1990 |
| JP | H05-154176 | 6/1993 |
| JP | H06-5614 | 1/1994 |
| JP | H06-502104 | 3/1994 |
| JP | H07-84697 | 9/1995 |
| JP | H08-510665 A | 11/1996 |
| JP | 8-322879 A | 12/1996 |
| JP | H10-95810 | 4/1998 |
| JP | H10-510743 | 10/1998 |
| JP | H11-512643 | 11/1999 |
| JP | 3091283 B2 | 7/2000 |
| JP | 2000-510376 | 8/2000 |
| JP | 2000-512886 | 10/2000 |
| JP | 2001-095845 | 4/2001 |
| JP | 2001-129019 A | 5/2001 |
| JP | 2001-328191 | 11/2001 |
| JP | 2002-508693 | 3/2002 |
| JP | 3262172 | 3/2002 |
| JP | 2002-528174 | 9/2002 |
| JP | 2002-537904 | 11/2002 |
| JP | 2003-024372 | 1/2003 |
| JP | 2003-052750 | 2/2003 |
| JP | 2004-500908 | 1/2004 |
| JP | 2004-049529 | 2/2004 |
| JP | 2005-504591 | 2/2005 |
| JP | 2005-095759 | 4/2005 |
| JP | 2005-193001 | 7/2005 |
| JP | 2005-525134 | 8/2005 |
| JP | 2006-501022 | 1/2006 |
| JP | 2006-510456 A | 3/2006 |
| JP | 2006-115996 | 5/2006 |
| JP | 2006-255051 | 9/2006 |
| JP | 2006-280526 | 10/2006 |
| JP | 2007-014705 | 1/2007 |
| JP | 2007-509695 | 4/2007 |
| JP | 2008-002034 | 1/2008 |
| JP | 2008-023311 | 2/2008 |
| JP | 2008-023365 | 2/2008 |
| JP | 2008-025078 | 2/2008 |
| JP | 2008-025079 | 2/2008 |
| JP | 2008-025080 | 2/2008 |
| JP | 2008-025081 | 2/2008 |
| JP | 2008-025082 | 2/2008 |
| JP | 2008-025083 | 2/2008 |
| JP | 2008-025084 | 2/2008 |
| JP | 2008-025085 | 2/2008 |
| JP | 2008-029830 | 2/2008 |
| JP | 2008-503323 | 2/2008 |
| JP | 2008-138340 | 6/2008 |
| JP | 2008-144322 | 6/2008 |
| JP | 2008-529721 | 8/2008 |
| JP | 2008-229032 | 10/2008 |
| JP | 2008-229033 | 10/2008 |
| JP | 2008-237569 | 10/2008 |
| JP | 2008-264084 | 11/2008 |
| JP | 2008-266813 | 11/2008 |
| JP | 2008-541943 | 11/2008 |
| JP | 2008-307179 | 12/2008 |
| JP | 2009-005767 | 1/2009 |
| JP | 2009-030218 | 2/2009 |
| JP | 2009-201878 | 9/2009 |
| JP | 2009-297048 | 12/2009 |
| JP | 2010-088822 | 4/2010 |
| JP | 2010-518918 | 6/2010 |
| JP | 2010-148708 | 7/2010 |
| JP | 2010-526629 | 8/2010 |
| JP | 2010-279568 | 12/2010 |
| JP | 2010-285735 | 12/2010 |
| JP | 2011-038211 | 2/2011 |
| JP | 2011-067484 | 4/2011 |
| JP | 2011-072650 | 4/2011 |
| JP | 2011-074515 | 4/2011 |
| JP | 2011-080178 | 4/2011 |
| JP | 2011-510801 | 4/2011 |
| JP | 2011-104001 | 6/2011 |
| JP | 2011-104059 | 6/2011 |
| JP | 2011-120696 | 6/2011 |
| JP | 4693847 | 6/2011 |
| JP | 2011-226010 | 11/2011 |
| JP | 2011-226011 | 11/2011 |
| JP | 2012-050626 | 3/2012 |
| JP | 5122007 B1 | 1/2013 |

(56) References Cited

FOREIGN PATENT DOCUMENTS

| WO | 93/01781 | | 2/1993 |
|---|---|---|---|
| WO | 94/27539 | A | 12/1994 |
| WO | 96/19173 | | 6/1996 |
| WO | 98/55158 | | 12/1998 |
| WO | 99/00093 | | 1/1999 |
| WO | 99/29274 | | 6/1999 |
| WO | 00/24351 | | 5/2000 |
| WO | 01/45757 | | 6/2001 |
| WO | 03/017900 | | 3/2003 |
| WO | 03/028776 | | 4/2003 |
| WO | 2004/030713 | | 4/2004 |
| WO | 2004/058119 | A1 | 7/2004 |
| WO | 2005/044164 | | 5/2005 |
| WO | 2006/009996 | | 1/2006 |
| WO | 2006-130646 | | 12/2006 |
| WO | 2008/072675 | | 6/2008 |
| WO | 2008/101163 | | 8/2008 |
| WO | 2008/139425 | | 11/2008 |
| WO | 2008/149771 | A1 | 12/2008 |
| WO | 2009/102837 | | 8/2009 |
| WO | 2012/133724 | A1 | 10/2012 |

OTHER PUBLICATIONS

International Search Report in corresponding PCT Application No. PCT/JP2012/082087 dated Mar. 19, 2013, 2 pages.
Written Opinion mailed Jul. 3, 2012 in corresponding International Application No. PCT/JP2012/058499.
International Search Report mailed Jul. 3, 2012 in corresponding International Application No. PCT/JP2012/058499.
Reply to Written Opinion dated Jan. 30, 2013, corresponds to International Application No. PCT/JP2012/058499.
Search Report mailed Jul. 17, 2012 in corresponding International Application No. PCT/JP2012/061505.
International International Search Report mailed Mar. 12, 2013 in corresponding International Application No. PCT/JP2012/082104.
International Search Report mailed Mar. 19, 2013 in corresponding International Application No. PCT/JP2013/054382.
International Search Report mailed May 21, 2014 in corresponding International Application No. PCT/JP2013/054796.
International Search Report mailed Jan. 8, 2013 in corresponding International Application No. PCT/JP2012/075583.
International Search Report mailed Jul. 2, 2013 in corresponding International Application No. PCT/JP2013/058860.
International Search Report mailed Jul. 2, 2013 in corresponding International Application No. PCT/JP2013/058861.
International Search Report mailed Jul. 2, 2013 in corresponding International Application No. PCT/JP2013/058862.
International Search Report mailed Jun. 18, 2013 in corresponding International Application No. PCT/JP2013/058855.
International Search Report mailed Mar. 26, 2013 in corresponding International Application No. PCT/JP2012/082977.
International Search Report mailed May 14, 2013 in corresponding International Application No. PCT/JP2013/058836.
International Search Report mailed May 21, 2013 in corresponding International Application No. PCT/JP2013/058859.

* cited by examiner

Fig.8
(a)
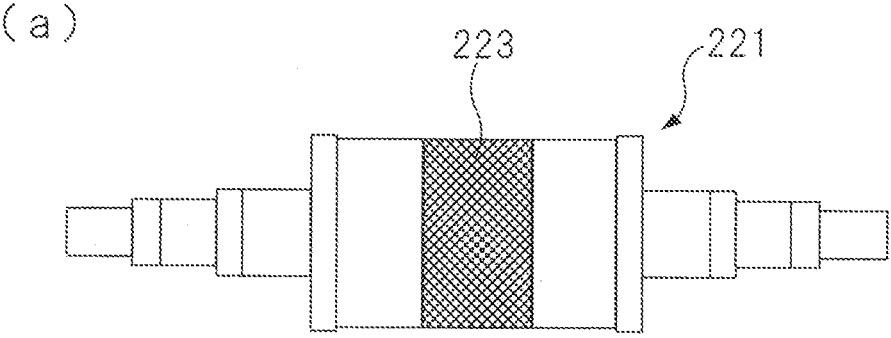
(b)
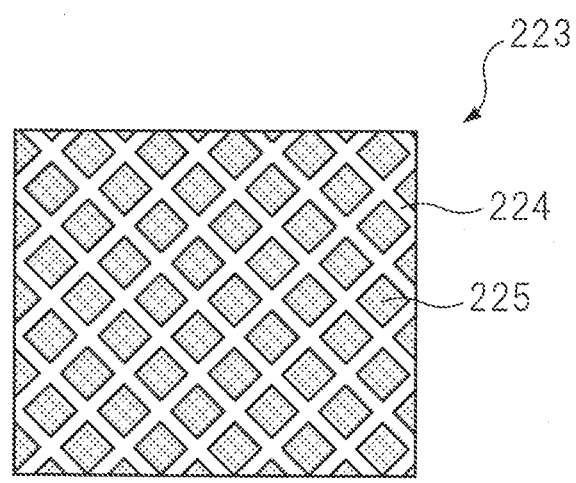
(c)
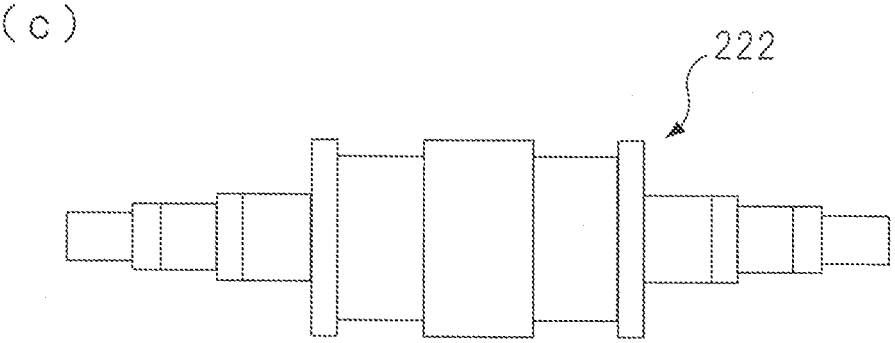

Fig.10
(a)
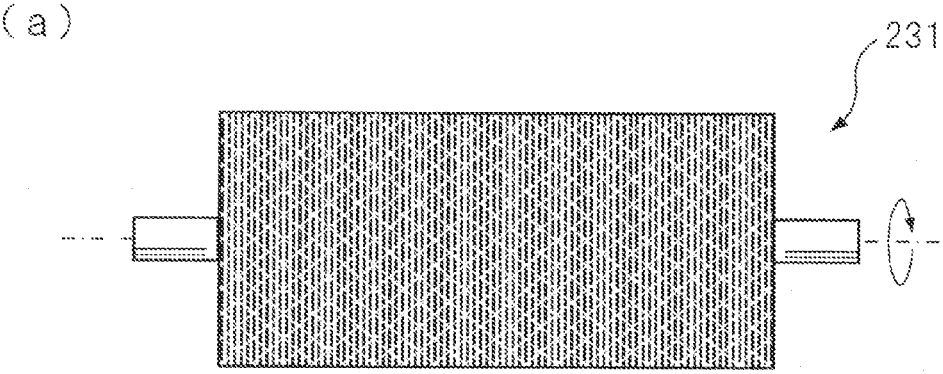
(b)
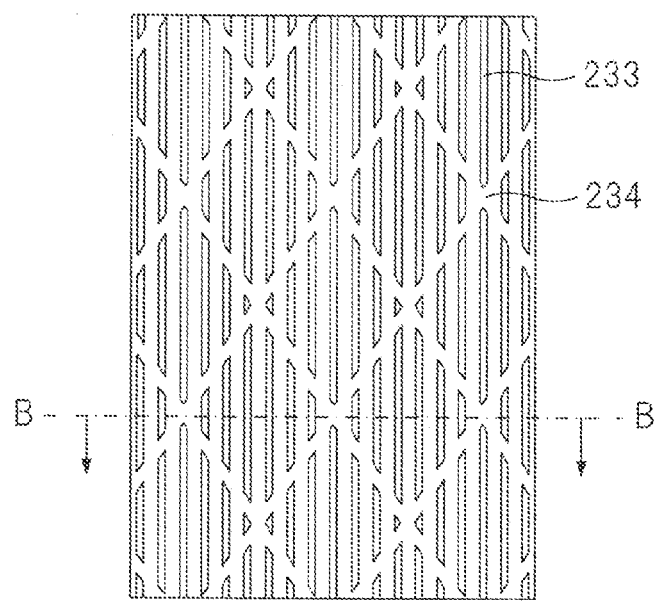
(c)
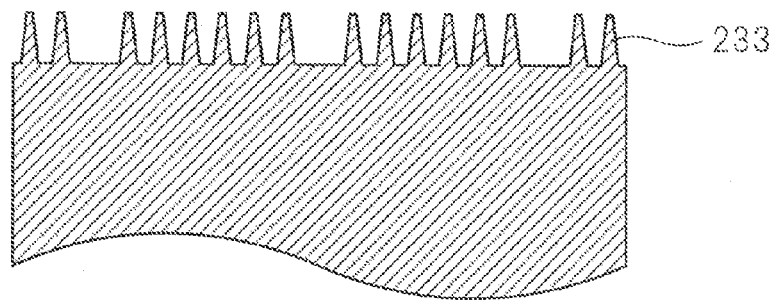

Fig.11
(a)
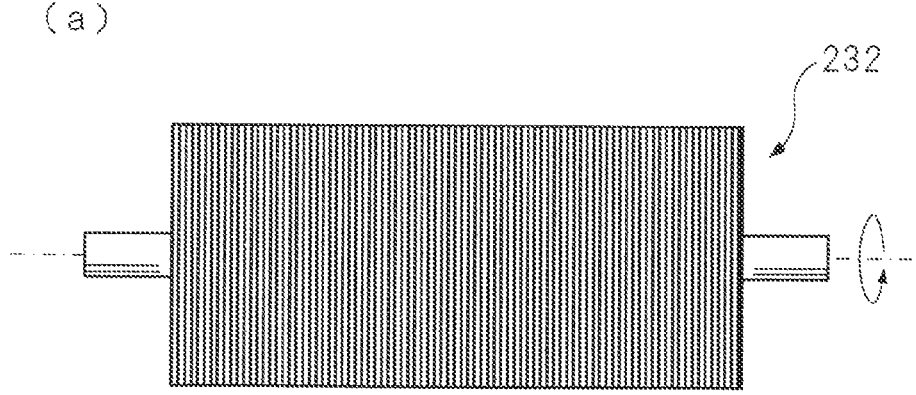
(b)
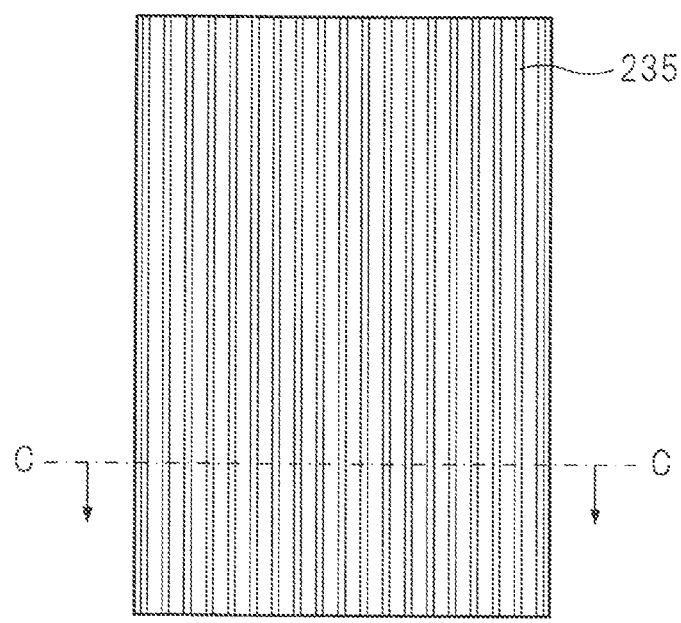
(c)
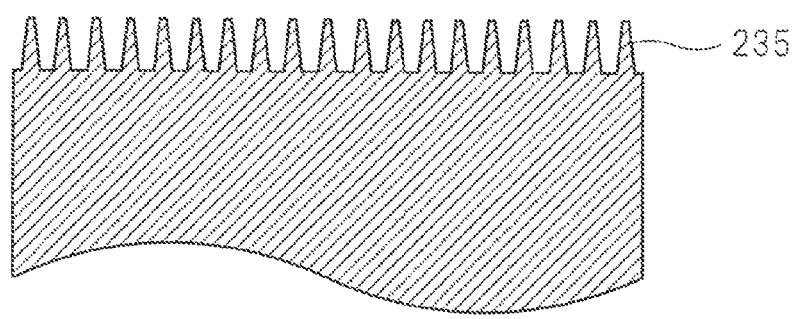

Fig.16
(a)
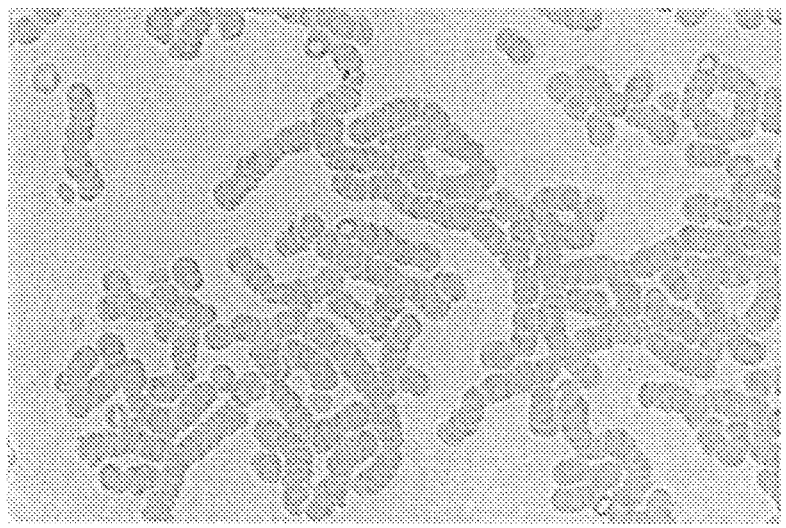
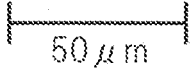
(b)
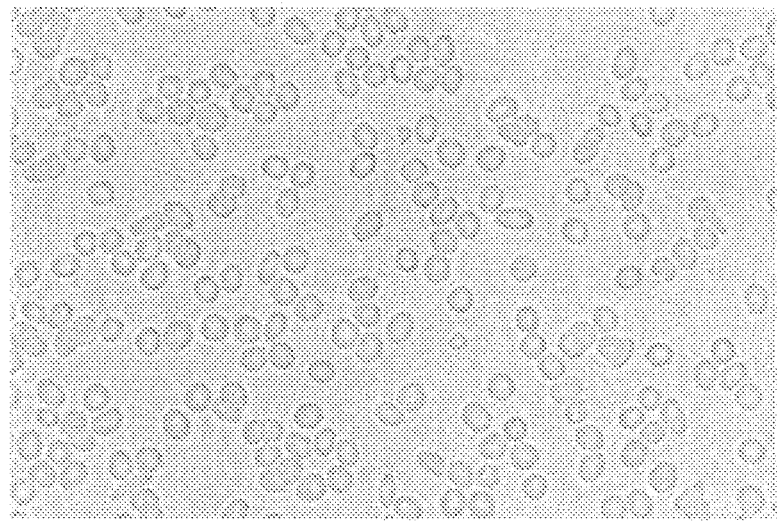
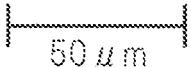

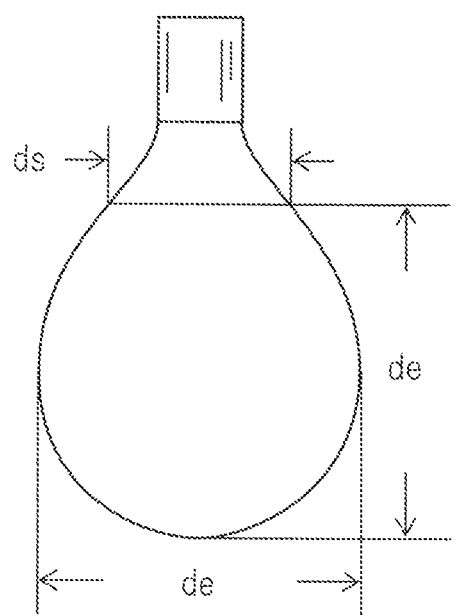

ABSORBENT ARTICLE

CROSS-REFERENCES TO RELATED APPLICATIONS

The present application is National Phase of International Application Number PCT/JP2012/082087 filed Dec. 11, 2012 and claims the priority of Japanese patent Application No. 2012-044439 filed Feb. 29, 2012.

TECHNICAL FIELD

The present invention relates to an absorbent article, such as a sanitary napkin, panty liner, incontinence pad or incontinence liner.

BACKGROUND ART

Sanitary napkins are known in the prior art which have a side panel made of a liquid-permeable perforated polymer film and a lining sheet (PTL 1, for example). There are also known as prior art, sanitary napkins that are provided with a central absorbent body section comprising a top sheet, a back sheet and an absorbent body, and a pair of flaps each comprising a top sheet and back sheet that extend outward from the center of both side sections of the central absorbent body section, wherein the top sheet is bonded with the back sheet at the borders between the central absorbent body and the flaps (PTL 2, for example).

CITATION LIST

Patent Literature

[PTL 1] Japanese Unexamined Patent Publication SHO No. 64-56051
[PTL 2] Japanese Patent Publication No. 3091283

SUMMARY OF THE INVENTION

Technical Problem

When pressure is applied to the absorbent body of an absorbent article, the body fluid that has been absorbed in the absorbent body often temporarily exudes from the edges in the widthwise direction of the absorbent body. When this occurs with a conventional absorbent article such as described in PTL 1, the body fluid that has exuded from the absorbent body permeates between the liquid-permeable perforated polymer film and the lining sheet at the side panels, often leaking from the widthwise direction of the absorbent article. With a conventional absorbent article such as described in PTL 2, on the other hand, the top sheet is bonded with the back sheet at the borders between the central absorbent body and the flaps, and therefore body fluid that has exuded from the absorbent body does not permeate between the top sheet and the back sheet at the flap sections. However, since body fluid that has exuded from the absorbent body at the edge sections in the widthwise direction of the absorbent body is temporarily blocked between the top sheet and the back sheet, it exudes out of the top sheet at the edge sections in the widthwise direction of the absorbent body, often leaking from the widthwise direction of the absorbent article.

It is an object of the present invention to provide an absorbent article that can help prevent body fluid that has exuded from the absorbent body, from leaking from the widthwise direction of the absorbent article under pressure applied to the absorbent article.

Solution to Problem

In order to solve the aforementioned problems, the invention employs the following construction.

Specifically, the invention is an absorbent article having a lengthwise direction and a widthwise direction, comprising a liquid-permeable top sheet provided on the skin side, a liquid-impermeable back sheet provided on the clothing side and a liquid-retaining absorbent body including the edges extending in the lengthwise direction on both sides in the widthwise direction and provided between the top sheet and the back sheet, there being included at least on the outer sides of both edges in the widthwise direction of the absorbent body, a plurality of first fluid channels and a plurality of second fluid channels for inflow of body fluid that has exuded from the absorbent body, the plurality of first fluid channels extending in the lengthwise direction and being aligned in the widthwise direction, and the plurality of second fluid channels connecting the adjacent first fluid channels.

Advantageous Effect of the Invention

According to the invention it is possible to prevent body fluid that has exuded from the absorbent body from leaking from the widthwise direction of the absorbent article under pressure applied to the absorbent article.

BRIEF DESCRIPTION OF DRAWINGS

FIG. 8 is a set of illustrations of a recess-forming roll to be used for production of an absorbent article according to an embodiment of the invention.

FIG. 10 is a set of illustrations of the upper roll of a stretching gear roll to be used for production of an absorbent article according to an embodiment of the invention.

FIG. 11 is a set of illustrations of the lower roll of a stretching gear roll to be used for production of an absorbent article according to an embodiment of the invention.

FIG. 16 is a pair of photomicrographs of menstrual blood containing and not containing a blood modifying agent.

FIG. 17 is a diagram illustrating a method of measuring surface tension.

DESCRIPTION OF EMBODIMENTS

Figure 1:
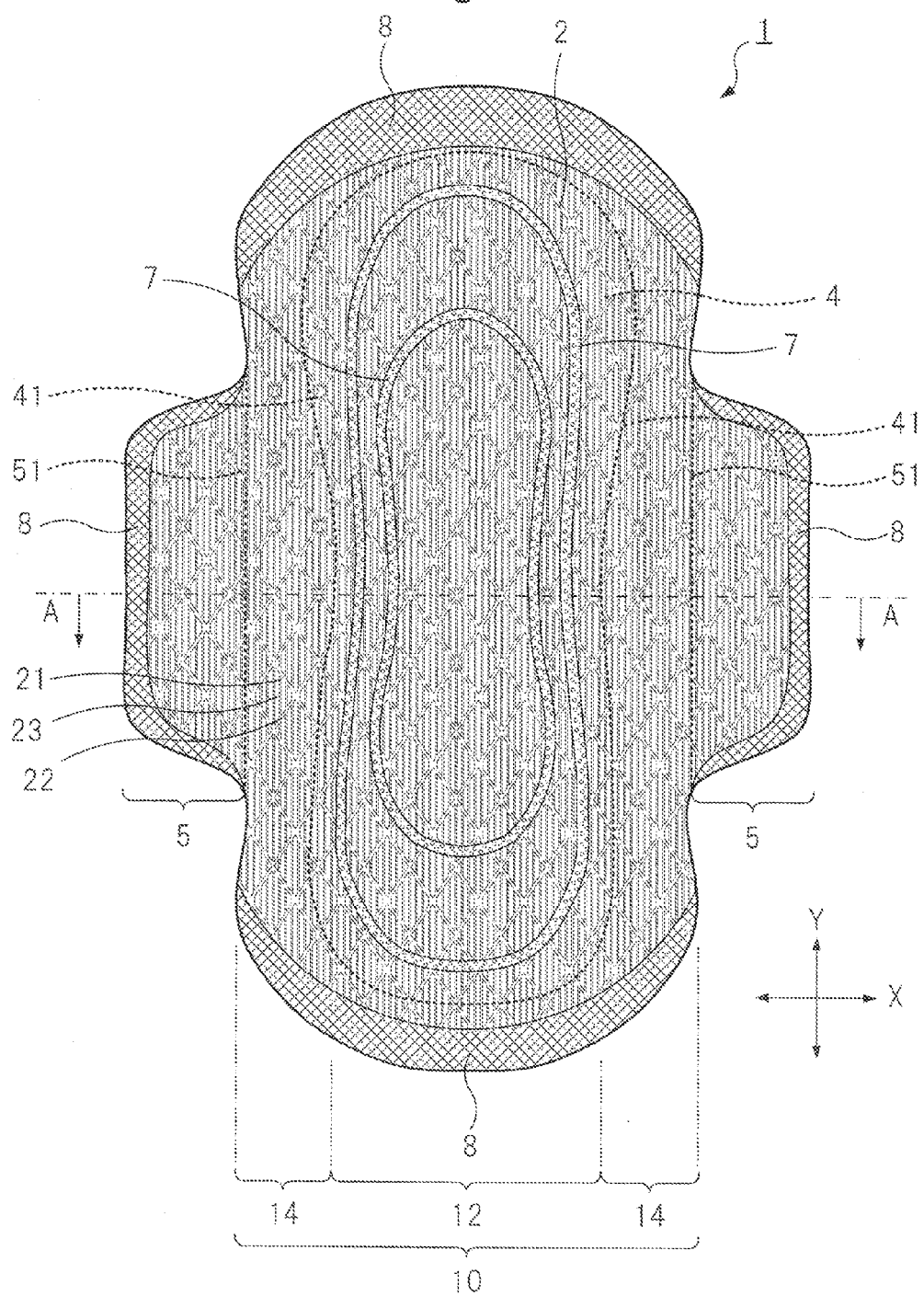
FIG. 1 is a plan view showing an embodiment of an absorbent article of the invention.

The invention will now be described with reference to the accompanying drawings, with the understanding that the invention is not limited to the examples depicted in the drawings.

Figure 2:
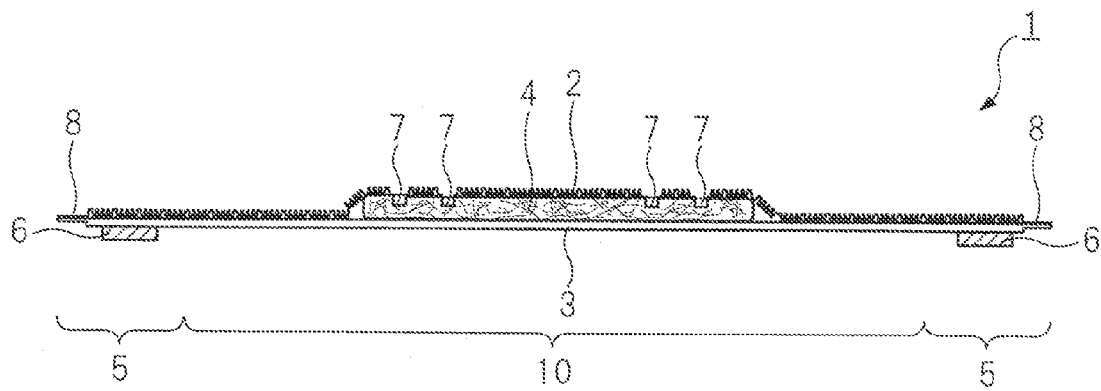
FIG. 2 is a simplified cross-sectional view showing a cross-section of FIG. 1 along line A-A.

FIG. 1 is plan view showing an absorbent article according to an embodiment of the invention, and FIG. 2 is a simplified cross-sectional view showing a cross-section of FIG. 1 along line A-A. The absorbent article 1 comprises a body section 10, having a liquid-permeable top sheet 2 provided on the skin side (the skin-contact side), a liquid-impermeable back sheet 3 provided on the clothing side (non-skin-contact side), and a liquid-retaining absorbent body 4 provided between the top sheet 2 and the back sheet 3, and a pair of wing sections 5 each having a top sheet 2 and a back sheet 3, provided on both sides of the body section 10 so as to extend in the widthwise direction from both edges of the body section 10. Numeral 51 denotes the base of each wing section 5 (the border between the body section 10 and each wing section 5). The surface of each wing section 5 on the side opposite the clothing side consists of the top sheet 2. A pressure-sensitive adhesive section 6 is provided on the clothing side of each wing section 5. In FIG. 1, the widthwise direction of the absorbent article 1 is the X direction, and the lengthwise direction is the Y direction. The planar direction of the absorbent article 1 is the XY direction.

The shape of the body section 10 is not particularly restricted so long as it is a shape suited to the female body and the shape of underwear, such as roughly rectangular, roughly elliptical or hourglass-shaped. The dimensions of extension in the lengthwise direction of the outer shape of the body section 10 are preferably 100 to 500 mm and more preferably 150 to 350 mm. The dimensions of extension in the widthwise direction of the outer shape of the body section 10 are preferably 30 to 200 mm and more preferably 40 to 180 mm.

The top sheet 2 transports body fluid such as urine and menstrual blood that has been excreted from a wearer into the absorbent body 4. At least a portion of the top sheet 2 has a liquid-permeable property, and has numerous openings formed for permeation of body fluid.

The top sheet 2 is made of a resin film. The resin film used as the top sheet 2 is composed of a copolymer of an olefin and another monomer such as an acrylic acid ester or vinyl acetate, or a polyolefin, polyester, polypropylene, polyethylene, polyethylene terephthalate, polyamide, cellulose acetate or the like. For high softness and reduced irritation to the skin, the resin film to be used as the top sheet 2 is most preferably a copolymer of an olefin and another monomer, or a polyolefin.

The basis weight of the top sheet 2 is preferably between 1 g/m$^2$ and 40 g/m$^2$, and more preferably between 10 g/m$^2$ and 35 g/m$^2$. The thickness of the resin film forming the top sheet 2 is preferably between 0.01 mm and 0.4 mm and more preferably between 0.1 mm and 0.35 mm. If the thickness of the resin film forming the top sheet 2 is less than 0.01 mm, the concealing property of the top sheet 2, described hereunder, may be too low, while if the thickness of the resin film forming the top sheet 2 exceeds 0.4 mm, the stiffness of the top sheet 2 may be increased and irritation by the top sheet 2 on the skin of the wearer may be too strong. Since the top sheet 2 has protrusions as explained below, the apparent thickness of the top sheet 2 is greater than the thickness of the resin film forming the top sheet 2. The apparent thickness of the top sheet 2 is preferably between 0.01 mm and 1 mm, and more preferably between 0.1 mm and 0.5 mm.

The top sheet 2 has a concealing property so that body fluids absorbed into the absorbent body 4 cannot be seen from the exterior. The concealing property of the top sheet 2 is produced by mixing a filler such as titanium oxide in a resin. When the filler is titanium oxide, the titanium oxide content is preferably at least 1% and no greater than 50%, and more preferably at least 3% and no greater than 15%, with respect to the weight of the resin film. If the titanium oxide content is less than 1% with respect to the weight of the resin film, the concealing effect of the top sheet 2 for body fluids absorbed into the absorbent body 4 may be too small. If the titanium oxide content exceeds 50% of the weight of the resin film, it may become difficult to form a sheet from the titanium oxide-containing resin.

The top sheet 2 has a plurality of first protrusions 21 that extend in the lengthwise direction and are aligned in the widthwise direction, a plurality of second protrusions 22 connecting the adjacent first protrusions 21, and bottom sections 23 which form the bases of the first protrusions 21 and second protrusions 22.

Figure 3:
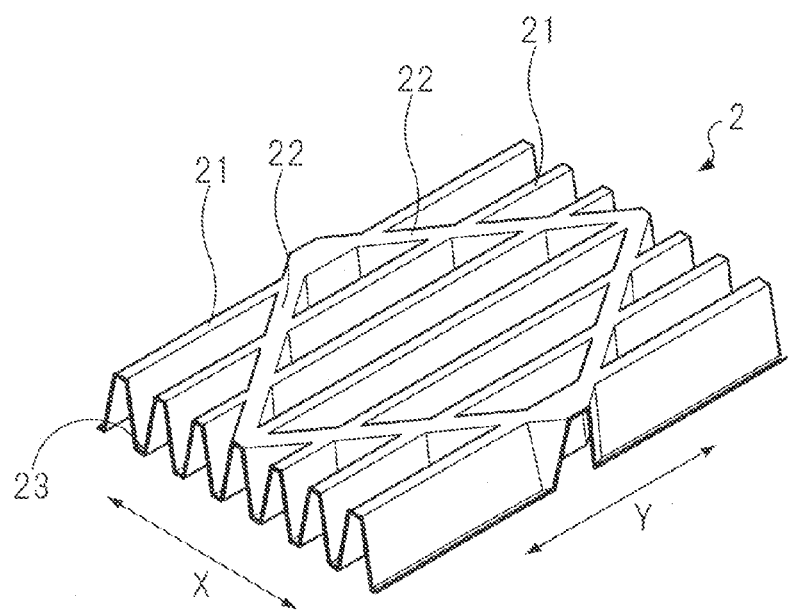
FIG. 3 is a diagram illustrating first protrusions, second protrusions and bottom sections formed in the top sheet of an absorbent article according to an embodiment of the invention, in the regions on the outer sides of both edges in the widthwise direction of the absorbent body of the body section of the top sheet, and in the wing sections.
Figure 4:
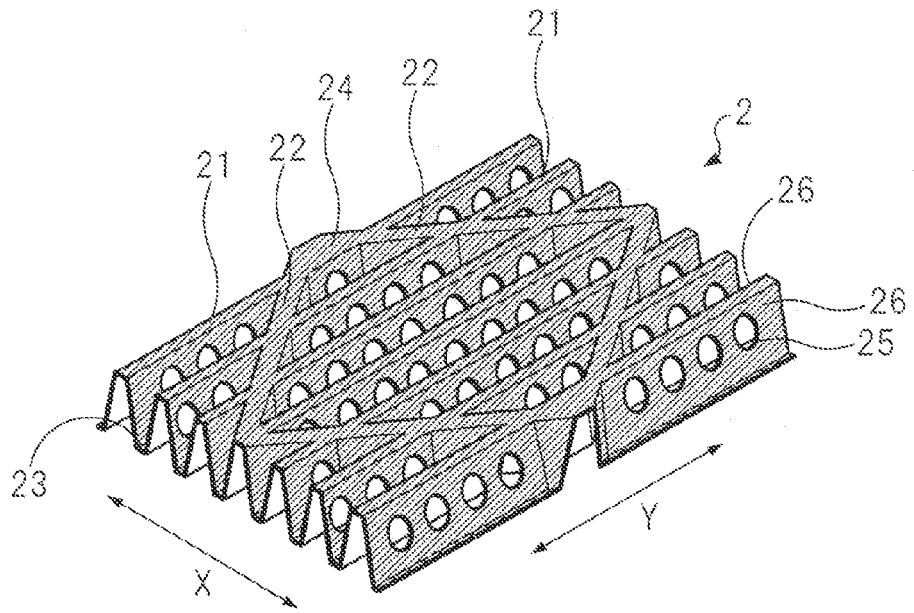
FIG. 4 is a diagram illustrating first protrusions, second protrusions and bottom sections formed in the top sheet of an absorbent article according to an embodiment of the invention, in the region in which the absorbent body is formed.

The first protrusions 21, second protrusions 22 and bottom sections 23 provided in the top sheet 2 will now be explained in detail with reference to FIG. 3 and FIG. 4. FIG. 3 is a diagram for illustration of the first protrusions, second protrusions and bottom sections formed in the regions 14 of the top sheet 2 of the body section 10 on the outer sides of both edges 41 in the widthwise direction of the absorbent body 4, and in the top sheet 2 of the wing sections 5 (see FIG. 1). FIG. 4 is a diagram for illustration of the first protrusions, second protrusions and bottom sections formed in the region 12 of the top sheet 2 of the body section 10 in which the absorbent body 4 is provided (see FIG. 1). The first protrusions, second protrusions and bottom sections formed in the regions 14 of the top sheet 2 of the body section 10 on the outer sides of both edges 41 in the widthwise direction of the absorbent body 4, and in the top sheet 2 of the wing sections 5, differ slightly from the first protrusions, second protrusions and bottom sections formed in the region 12 of the top sheet 2 of the body section 10 where the absorbent body 4 is provided, as described below.

As shown in FIG. 3, in the regions 14 on the outer sides of both edges 41 in the widthwise direction of the absorbent body 4 and in the wing sections 5, the top sheet 2 comprises a plurality of first protrusions 21 that extend in the lengthwise direction (Y direction) and are aligned in the widthwise direction (X direction). The cross-sectional shapes of the first protrusions 21 are, for example, approximate upside-down U-shapes (hereunder referred to as "approximate U-shapes"). "Approximate U-shapes" include U-shapes, as well as shapes that become U-shapes by modifications such as by rounding corners or curving straight lines. For example, "approximate U-shapes" include V-shaped and inverted M-shaped forms, as well as trapezoids.

The adjacent first protrusions 21 are connected through the plurality of second protrusions 22. The second protrusions 22 preferably extend in a direction diagonal to the first protrusions 21 that extend in the lengthwise direction (Y direction). For example, the angle formed between the first protrusions 21 and the second protrusions 22 is preferably between 10° and 170°. The cross-sectional shapes of the second protrusions 22, as observed by cutting the second protrusions 22 in the direction perpendicular to the direction in which the second protrusions 22 extend may be, for example, approximate inverted V-shapes.

Figure 5:
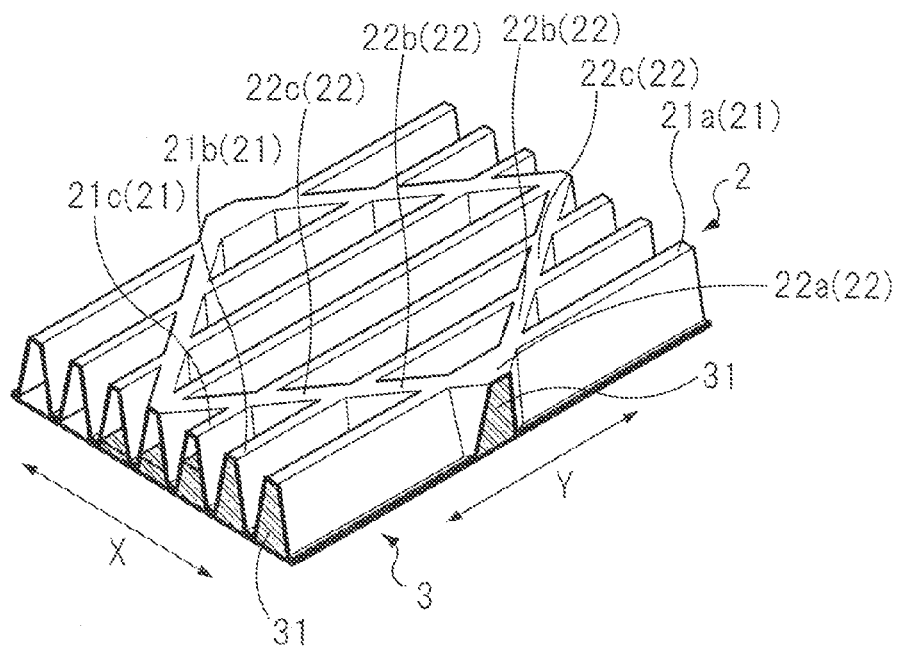
FIG. 5 is a diagram illustrating fluid channels formed by the protrusions of the top sheet, and the back sheet.

FIG. 5 is a diagram illustrating fluid channels formed by the protrusions 21,22 of the top sheet 2, and the back sheet 3. As shown in FIG. 5, a hollow structure is formed by combination of the first protrusions 21 and second protrusions 22 with the back sheet 3 described below. Body fluid 31 that has exuded from the absorbent body 4 flows through the hollow structure. That is, the first protrusions 21 and second protrusions 22, together with the back sheet 3 described below, form fluid channels for flow of body fluid 31.

For example, body fluid 31 that has been exuded from the absorbent body 4 and has then flowed into the fluid channels formed by the second protrusion 22a and back sheet 3 flows into the fluid channel formed by the first protrusion 21a and the back sheet 3. Body fluid that has flowed into the fluid channel formed by the first protrusion 21a and the back sheet 3 flows in the lengthwise direction (Y direction) through the fluid channel formed by the first protrusion 21a and the back sheet 3. After having flowed in the lengthwise direction (Y direction), the body fluid 31 flows into the fluid channel formed by the adjacent first protrusion 21b and the back sheet 3, through the fluid channel formed by the second protrusion 22b and the back sheet 3. Body fluid that has flowed into the fluid channel formed by the first protrusion 21b and the back sheet 3 flows in the lengthwise direction (Y direction) through the fluid channel formed by the first protrusion 21b and the back sheet 3. After having flowed in the lengthwise direction (Y direction), the body fluid 31 flows into the fluid channel formed by the adjacent first protrusion 21c and the back sheet 3, through the fluid channel formed by the second protrusion 22c and the back sheet 3. By such repetition of flow of the body fluid 31 in the lengthwise direction (Y direction) through the fluid channels formed by the first protrusions 21 and the back sheet 3, and subsequent flow of the body fluid 31 into the fluid channels formed by the adjacent first protrusions 21 and the back sheet 3 through the fluid channels formed by the second protrusions 22 and the back sheet 3, the body fluid that has exuded from the absorbent body 4 spreads in the widthwise direction (X direction) between the top sheet 2 and the back sheet 3.

Figure 6:
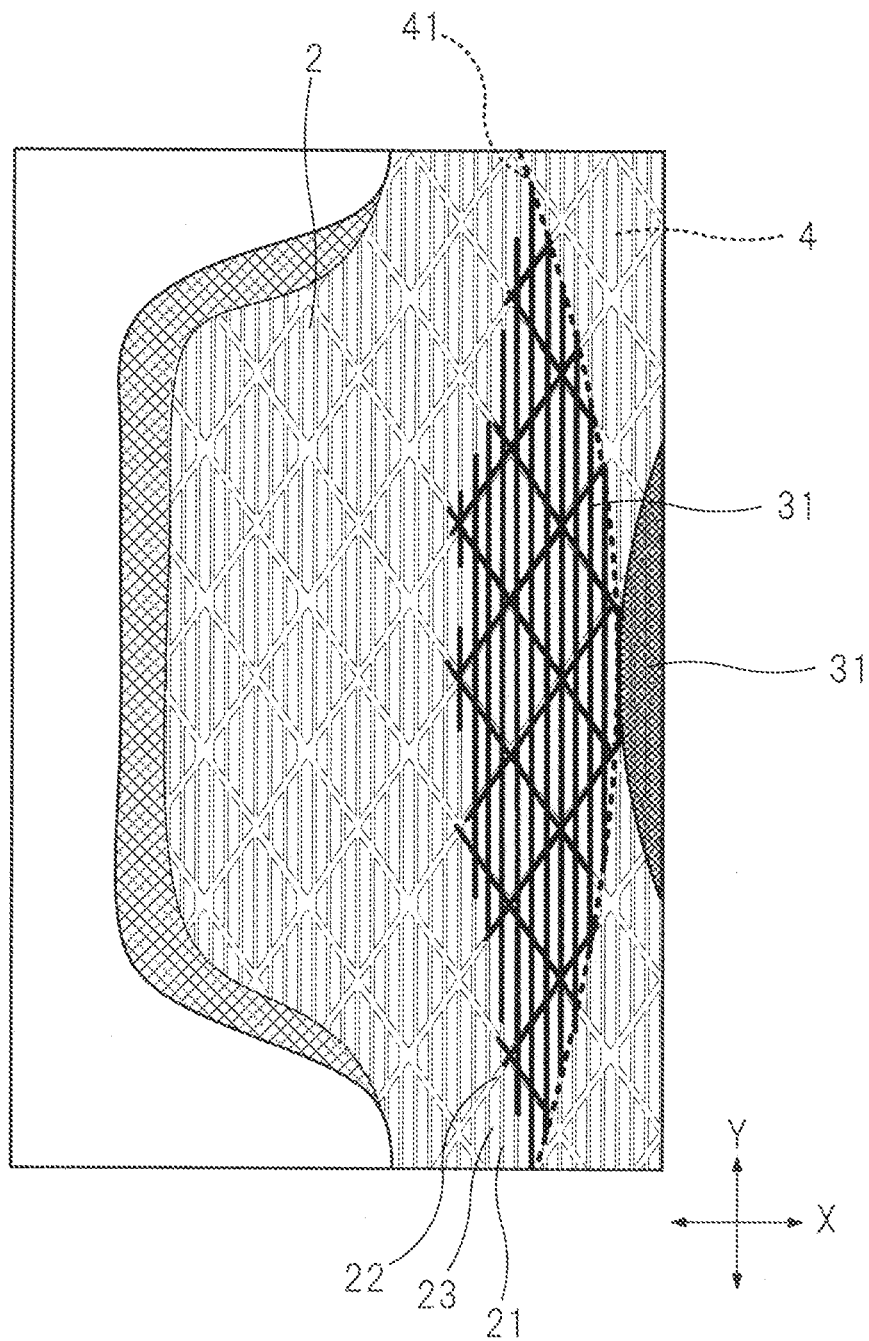
FIG. 6 is a diagram illustrating body fluid of a wearer that has exuded from the absorbent body and flowed into fluid channels.

As shown in FIG. 6, the body fluid 31 that has exuded from the absorbent body 4, after having been spread in the lengthwise direction (Y direction) by the fluid channels formed by the first protrusions 21 of the top sheet 2 and the back sheet, then spreads in the widthwise direction (X direction) by the fluid channels formed by the second protrusions 22 of the top sheet 2 and the back sheet. Thus, in order for body fluid 31 that has exuded from the absorbent body 4 to spread in the widthwise direction (X direction), a large amount of body fluid must exude from the absorbent body 4. Consequently, this can help prevent body fluid 31 that has exuded from the absorbent body 4 from spreading in the widthwise direction (X direction), and can help prevent body fluid 31 that has exuded from the absorbent body 4 from leaking from the widthwise direction of the absorbent article 1 under pressure applied to the absorbent article 1.

The number of first protrusions 21 per 1 cm in the widthwise direction is preferably 3 or greater and more preferably 5 or greater. If the number of first protrusions 21 per 1 cm in the widthwise direction is 2 or less, a smaller amount of body fluid will be able to accumulate in the first protrusions 21, and body fluid that has exuded from the absorbent body may leak from the widthwise direction of the absorbent article.

The lengths of the second protrusions 22 in the lengthwise direction (Y direction) are preferably between 0.3 mm and 5 mm and more preferably between 0.5 mm and 3 mm. If the length of the second protrusions 22 in the lengthwise direction (Y direction) are smaller than 0.3 mm, body fluid that has flowed into the first protrusions 21 will not easily flow into the adjacent first protrusions 21 through the second protrusions 22, and the blocked body fluid may exude out of the top sheet 2. Also, if the lengths of the second protrusions 22 in the lengthwise direction (Y direction) are greater than 5 mm, body fluid that has flowed into the first protrusions 21 may flow into the adjacent first protrusions 21 through the second protrusions 22 before flowing in the lengthwise direction (Y direction) in the first protrusions 21, and body fluid that has exuded from the absorbent body may leak from the widthwise direction of the absorbent article.

By providing first protrusions 21 and second protrusions 22 in the top sheet 2 of the wing sections 5, the first protrusions 21 and second protrusions 22 are present at the folded sections formed when the wing sections 5 are folded to anchor the absorbent article 1 to underwear. The first protrusions 21 and second protrusions 22 impart a soft feel on the skin to the surface of the absorbent article 1. This results in satisfactory skin feel at the leg sections of underwear when the absorbent article 1 is covered by worn underwear.

As shown in FIG. 4, the top sheet 2 at region 12 of the body section 10 where the absorbent body 4 is provided comprises first protrusions 21, second protrusions 22 and bottom sections 23, similar to the top sheet 2 at the regions 14 on the outer sides of both edges 41 in the widthwise direction of the absorbent body 4 of the body section 10, and at the wing sections 5. However, the first protrusions 21, second protrusions 22 and bottom sections 23 of the top sheet 2 in the region 12 of the body section 10 in which the absorbent body 4 is provided further comprise a blood modifying agent layer 24, described below, on the skin side surface. The first protrusions 21 of the top sheet 2 in the region 12 in which the absorbent body 4 is provided also further comprise openings 25, described below.

The first protrusions 21 of the top sheet 2 in the region 12 of the body section 10 in which the absorbent body 4 is provided have a plurality of openings 25 aligned in the lengthwise direction (Y direction), on both sides 26. Body fluid of a wearer, discharged into the top sheet 2 at the region 12 of the body section 10 in which the absorbent body 4 is provided, migrates through the openings 25 into the absorbent body 4. Also, body fluid of the wearer discharged into the top sheet 2 rapidly collects toward the bottom sections 23 due to the approximately U-shaped sections in the widthwise direction (X direction) formed by every two adjacent first protrusions 21 and the bottom sections 23. The body fluid flowing toward the bottom sections 23 passes through the openings 25 formed on the sides 26 of the first protrusions 21 before reaching the bottom sections 23, and flows into the absorbent body 4. Body fluid that has collected at the bottom sections 23 also passes through the openings 25 formed on the sides 26 of the first protrusions 21 and flows into the absorbent body 4.

Body fluid of the wearer is therefore rapidly absorbed into the absorbent body 4 through the openings 25 provided on the sides 26 of the first protrusions 21. The amount of body fluid residing in the top sheet 2 can also be reduced by the openings 25 formed in the sides 26 of the first protrusions 21.

A blood modifying agent may also be coated on the surface of the skin side of the top sheet 2, at the region 12 of the body section 10 in which the absorbent body 4 is provided, to form a blood modifying agent layer 24 on the surface of the skin-contact side of the top sheet 2. The blood modifying agent layer 24 can reduce residue of body fluids from the wearer, and especially highly viscous menstrual blood, on the surface of the top sheet 2. The blood modifying agent layer 24 will be described in detail below.

The contact area between the skin of the wearer and the top sheet 2 is reduced by the first protrusions 21 provided on the top sheet 2 in the region 12 of the body section 10 in which the absorbent body 4 is provided, and therefore the feel of the top sheet 2 on the skin is satisfactory. Incidentally, the first protrusions alone may be formed on the top sheet 2 in the region 12 of the body section 10 in which the absorbent body 4 is provided, without forming any second protrusions. This will also reduce the contact area between the skin of the wearer and the top sheet 2, thus resulting in a satisfactory feel of the top sheet 2 on the skin. However, since the first protrusions are more resistant to collapse if second protrusions are provided, it is preferred to form both the first protrusions and second protrusions on the top sheet 2 in the region 12 of the body section 10 in which the absorbent body 4 is provided.

The back sheet 3 shown in FIG. 1 and FIG. 2 prevents body fluid that has been absorbed into the absorbent body 4 from leaking to the outside. A material that is impermeable to body fluids is used for the back sheet 3. The material used for the back sheet 3 may be, for example, a hydrophobic nonwoven fabric, an impermeable plastic film or nonwoven fabric of polyethylene, polypropylene or the like, or a laminate sheet with an impermeable plastic film. The material used for the back sheet 3 may also be an SMS nonwoven fabric obtained by sandwiching a highly water-resistant meltblown nonwoven fabric between high-strength spunbond nonwoven fabrics. By using a material which is not permeable to body fluids as the back sheet 3, it is possible to reduce mustiness during wearing.

At the sections where the back sheet 3 and top sheet 2 overlap, the back sheet 3, together with the first protrusions 21 and second protrusions 22 formed in the top sheet 2 described above, forms fluid channels for flow of body fluid 31. The back sheet 3 may also be bonded with the bottom sections 23 of the top sheet 2 using an adhesive such as a hot-melt adhesive.

The absorbent body 4 absorbs and retains body fluids. The absorbent body 4 preferably has high bulk, is resistant to deformation and has low chemical irritation. For example, the absorbent body 4 may be a composite absorbent body composed of fluffy pulp or an airlaid nonwoven fabric, and a super-absorbent polymer (SAP). The composite absorbent body may also be covered with a liquid-permeable material such as a tissue.

Instead of fluffy pulp in the composite absorbent body, there may be used, for example, artificial cellulose fiber such as chemical pulp, cellulose fiber, rayon or acetate. The basis weight of the absorbent fiber such as pulp in the composite absorbent body is preferably at least 100 g/m$^2$ and no greater than 800 g/m$^2$, and the mass ratio of the super-absorbent polymer in the composite absorbent body is preferably at least 10% and no greater than 65%, with the absorbent fiber defined as 100%. The basis weight of the liquid-permeable material, such as a tissue, covering the composite mixture is preferably at least 12 g/m$^2$ and no greater than 30 g/m$^2$.

An airlaid nonwoven fabric for the composite mixture may be, for example, a nonwoven fabric comprising pulp and synthetic fiber heat sealed together, or a nonwoven fabric comprising pulp and synthetic fiber fixed with a binder.

The super-absorbent polymer of the composite absorbent body has a three-dimensional network structure with appropriate crosslinking of a water-soluble polymer. The absorbent polymer absorbs 30 to 60 times the amount of water relative to the volume of the absorbent polymer before absorption of water. However, the absorbent polymer is essentially water-insoluble. The absorbent polymer does not exude absorbed water even when a moderate degree of pressure is applied. The absorbent polymer used is, for example, a starch-based, acrylic acid-based or amino acid-based particulate or filamentous polymer.

The shape and structure of the absorbent body 4 may be varied if necessary, but the total absorption by the absorbent body 4 must be suitable for the designed insertion volume and the desired use of the absorbent article 1. The size and absorbing power of the absorbent body 4 will also vary depending on the intended use.

As shown in FIG. 1, the edges 41 of the absorbent body 4 in the widthwise direction are curved so as to protrude inward in the widthwise direction (X direction). As shown in FIG. 6, this causes the first protrusions 21 provided on the top sheet 2 in the region 14 on the outer sides of both edges 41 in the widthwise direction of the absorbent body 4, extending in the lengthwise direction (Y direction), to reach to the edge 41 of the absorbent body 4 in the widthwise direction. Thus, body fluid 31 that has exuded from the absorbent body 4, and is flowing in the lengthwise direction (Y direction) through the fluid channels formed by the first protrusions 21 and the back sheet, is re-absorbed into the absorbent body 4. This reduces the amount of body fluid flowing into the fluid channels formed by the adjacent first protrusions 21 and the back sheet 3, through the fluid channels formed by the second protrusions 22 and the back sheet 3, and further helps to prevent body fluid 31 that has exuded from the absorbent body 4 from leaking from the widthwise direction of the absorbent article 1 under pressure exerted on the absorbent article 1.

The absorbent body 4 is attached to the back sheet 3 using a hot-melt adhesive. This can inhibit peeling of the absorbent body 4 from the back sheet 3.

The wing sections 5 are provided in the absorbent article 1 to stably anchor the absorbent article 1 to underwear. After the wing sections 5 have been folded on the outer side of the underwear, they are attached to the crotch section of the underwear through the pressure-sensitive adhesive section 6 to allow the absorbent article 1 to be stably anchored to the underwear.

The pressure-sensitive adhesive section 6 anchors the absorbent article 1 to the crotch section of the underwear. The pressure-sensitive adhesive used to form the pressure-sensitive adhesive section 6 is preferably, for example, one composed mainly of a styrene-based polymer, tackifier or plasticizer. Styrene-based polymers include styrene-ethylene-butylene-styrene block copolymer, styrene-butylene polymer, styrene-butylene-styrene block copolymer and styrene-isobutylene-styrene copolymer, any of which may be used alone or as polymer blends of two or more. Styrene-ethylene-butylene-styrene block copolymer is preferred among these from the viewpoint of satisfactory thermostability.

The tackifier and plasticizer mentioned above are preferably solids at ordinary temperature, and these include tackifiers such C5 petroleum resin, C9 petroleum resin, dicyclopentadiene-based petroleum resin, rosin-based petroleum resin, polyterpene resin, terpenephenol resin and the like, and plasticizers such as monomer plasticizers including tricresyl phosphate, dibutyl phthalate and dioctyl phthalate, and polymer plasticizers including vinyl polymers and polyesters.

As shown in FIG. 1 and FIG. 2, the top sheet 2 and absorbent body 4 have compressed grooves 7 from the top sheet 2 to the interior of the absorbent body 4, formed by compression in the thickness direction by embossing. The compressed grooves 7 help prevent body fluid that has been discharged into the center section of the absorbent article 1 (the section corresponding to the body fluid excretion hole of the wearer) from diffusing in the widthwise direction (X direction). This can inhibit peeling of the top sheet 2 from the absorbent body 4. The compressed grooves 7 have continuous annular shapes, surrounding the center section of the absorbent article 1. The compressed grooves 7 surrounding the center section of the absorbent article 1 may be partially interrupted. That is, the compressed grooves 7 may have discontinuous annular shapes.

Also, compressed bonding of the top sheet 2 to the back sheet 3 by heat embossing forms seal sections 8 on both sides in the lengthwise direction and both sides in the widthwise direction of the absorbent article 1. This can prevent the top sheet 2 from peeling from the back sheet 3. Also, the seal sections 8 on both sides in the lengthwise direction allow both ends of the fluid channels formed by the first protrusions 21 and the back sheet 3 to be sealed by compression. Since this blocks both ends of the fluid channels formed by the first protrusions 21 and the back sheet 3, this can prevent body fluid of the wearer, that has flowed in a large amount into the fluid channels formed by the first protrusions 21 and the back sheet 3, from leaking from both edges in the lengthwise direction of the absorbent article 1.

The blood modifying agent in the blood modifying agent layer 24 has an Inorganic-Organic Balance (IOB) of 0.00-0.60, a melting point of no higher than 45° C., and a water solubility of no greater than 0.05 g at 25° C. in 100 g of water.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725 which is incorporated by reference herein.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |

TABLE 1-continued

| Group | Inorganic value | Organic value |
|---|---|---|
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

In the blood modifying agent, the IOB is about 0.00-0.60, preferably about 0.00-0.50, more preferably about 0.00-0.40 and even more preferably about 0.00-0.30. This is because a lower IOB is associated with higher organicity and higher affinity with blood cells.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood modifying agent has a melting point of no higher than about 45° C., it may be either liquid or solid at room temperature, or in other words, the melting point may be either about 25° C. or higher or below about 25° C., and for example, it may have a melting point of about −5° C. or about −20° C. The reason for a melting point of no higher than about 45° C. for the blood modifying agent will be explained below.

The blood modifying agent does not have a lower limit for its melting point, but its vapor pressure is preferably low. The vapor pressure of the blood modifying agent is preferably between about 0 and about 200 Pa, more preferably between about 0 and about 100 Pa, more preferably between about 0 and about 10 Pa, even more preferably between about 0 and about 1 Pa and yet more preferably between about 0.0 and about 0.1 Pa, at 25° C. (1 atmosphere). Considering that the absorbent article of the present disclosure is to be used in contact with the human body, the vapor pressure is preferably between about 0 and about 700 Pa, more preferably between about 0 and about 100 Pa, more preferably between about 0 and about 10 Pa, even more preferably between about 0 and about 1 Pa and yet more preferably between about 0.0 and about 0.1 Pa, at 40° C. (1 atmosphere). If the vapor pressure of the blood modifying agent is high, gasification may occur during storage and the amount may be reduced, often creating problems such as odor during wear.

The melting point of the blood modifying agent may also differ depending on the weather or duration of wear. For example, in regions with a mean atmospheric temperature of no higher than about 10° C., using a blood modifying agent with a melting point of no higher than about 10° C. may allow the blood modifying agent to stably modify blood after excretion of menstrual blood, even if it has been cooled by the ambient temperature.

Also, as the absorbent article may be used for a prolonged period of time, the melting point of the blood modifying agent is preferably at the high end of the range of no higher than about 45° C. This is because the blood modifying agent is not easily affected by sweat or friction during wearing, and will not easily migrate even during prolonged wearing.

The water solubility of 0.00-0.05 g may be measured by adding 0.05 g of sample to 100 g of deionized water at 25° C., allowing it to stand for 24 hours, and after 24 hours, gently stirring if necessary, and then visually evaluating whether or not the sample has dissolved.

As used herein, the term "solubility" in regard to water solubility includes cases where the sample completely dissolves in deionized water to form a homogeneous mixture, and cases where the sample is completely emulsified. As used herein, "completely" means that no mass of the sample remains in the deionized water.

When top sheet surfaces are coated with surfactants in order to alter the surface tension of blood and promote the rapid absorption of blood, because surfactants generally have high water solubility, the surfactant-coated top sheet is highly miscible with hydrophilic components (such as blood plasma) in the blood and therefore, instead, they tend to cause residue of blood on the top sheet. The aforementioned blood modifying agent has low water solubility and therefore, it does not cause residue of blood on the top sheet and allows rapid migration into the absorbent body.

As used herein, a water solubility of water at 25° C. may be simply referred to as "water solubility".

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.
Columns: SHODEX KF-801, KF-803 and KF-804, by Showa Denko K.K.
Eluent: THF
Flow rate: 1.0 mL/min
Driving volume: 100 µL
Detection: RI (differential refractometer)

The weight-average molecular weights listed in the examples of the present specification were measured under the conditions described below.

Preferably, the blood modifying agents is selected from the group consisting of the following items (i)-(iii), and any combination thereof:

(i) a hydrocarbon;
(ii) a compound having (ii-1) a hydrocarbon moiety, and (ii-2) one or more groups each selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more groups each selected from the group consisting of carbonyl group (—CO—) and oxy group (—O—) inserted between a C—C single bond of the hydrocarbon moiety, and (iii-3) one or more groups each selected from the group consisting of carboxyl group (—COOH) and hydroxyl group (—OH) substituting a hydrogen of the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds each selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy group (—O—) are inserted in the compounds of (ii) and (iii) above, the oxy group (—O—) are not adjacent to each other. Thus, compounds (ii) and (iii) do not include compounds with continuous oxy group (i.e., peroxides).

In the compounds of (iii), compounds in which at least one hydrogen on the hydrocarbon moiety is substituted with a hydroxyl group (—OH) are more preferred than compounds in which at least one hydrogen on the hydrocarbon moiety is substituted with a carboxyl group (—COOH). As shown in Table 1, the carboxyl groups bond with metals and the like in menstrual blood, drastically increasing the inorganic value from 150 to 400 or greater, and therefore a blood modifying agent with carboxyl groups can increase the IOB value to more than about 0.6 during use, potentially lowering the affinity with blood cells.

More preferably, the blood modifying agent is a compound selected from the group consisting of the following items (i')-(iii'), and any combination thereof:

(i') a hydrocarbon;
(ii') a compound having at least(ii'-1) a hydrocarbon moiety, and (ii'-2) one or more bonds each selected from the group consisting of carbonyl bond (—CO—), at least one ester bond (—COO—), at least one carbonate bond (—OCOO—), and/or at least one ether bond (—O—) inserted between a C—C single bond of the hydrocarbon moiety; and
(iii') a compound having at least (iii'-1) a hydrocarbon moiety, (iii'-2) one or more bonds each selected from the group consisting of carbonyl bond (—CO—), at least one ester bond (—COO—), at least one carbonate bond (—OCOO—), and/or at least one ether bond (—O—) inserted between a C—C single bond of a hydrocarbon, and (iii'-3) one or more groups each selected from the group consisting of carboxyl group (—COOH) and hydroxyl group (—OH) substituting a hydrogen on the hydrocarbon moiety.

When 2 or more same or different bonds are inserted in the compound of (ii') or (iii'), i.e., when 2 or more bonds each selected from the group consisting of carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood modifying agent is more preferably a compound with no more than about 1.8 carbonyl bonds (—CO—), no more than 2 ester bonds (—COO—), no more than about 1.5 carbonate bonds (—OCOO—), no more than about 6 ether bonds (—O—), no more than about 0.8 carboxyl groups (—COOH) and/or no more than about 1.2 hydroxyl groups (—OH), per 10 carbon atoms in the hydrocarbon moiety.

Even more preferably, the blood modifying agent may also be selected from the group consisting of the following items (A)-(F), and any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;

(B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted in-between a C—C single bond of the chain hydrocarbon moiety;

(E) a polyoxy $C_2$-$C_6$ alkylene glycol, or alkyl ester or alkyl ether thereof; and (F) a chain hydrocarbon.

The blood modifying agent in accordance with (A) to (F) will now be described in detail.

[(A) Ester of (A1) a Compound Having a Chain Hydrocarbon Moiety and 2-4 Hydroxyl Groups Substituting Hydrogens on the Chain Hydrocarbon Moiety, and (A2) a Compound Having a Chain Hydrocarbon Moiety and 1 Carboxyl Group Substituting a Hydrogen on the Chain Hydrocarbon Moiety]

The (A) ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety (hereunder also referred to as "compound (A)") includes esters of a compound with 4, 3 or 2 hydroxyl groups and a compound with 1 carboxyl group, and it is not necessary for all of the hydroxyl groups to be esterified so long as the IOB, melting point and water solubility are within the aforementioned ranges.

Examples of (A1) a compound having a chain hydrocarbon moiety and 2-4 hydroxyl groups substituting hydrogens on the chain hydrocarbon moiety (hereunder also referred to as "compound (A1)") include chain hydrocarbon tetraols such as alkanetetraols, including pentaerythritol, chain hydrocarbon triols such as alkanetriols, including glycerins, and chain hydrocarbon diols such as alkanediols, including glycols. Examples of (A2) a compound having a chain hydrocarbon moiety and 1 carboxyl group substituting a hydrogen on the chain hydrocarbon moiety (hereunder also referred to as "compound (A2)") include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acids.

[($a_1$) Ester of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

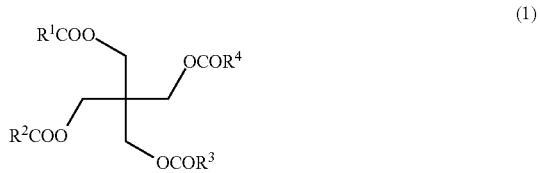

triesters of pentaerythritol and fatty acids, represented by the following formula (2):

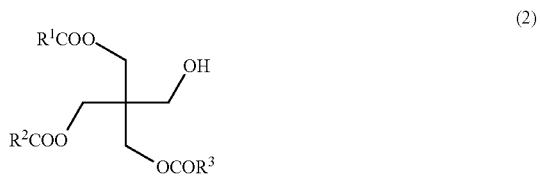

diesters of pentaerythritol and fatty acids, represented by the following formula (3):

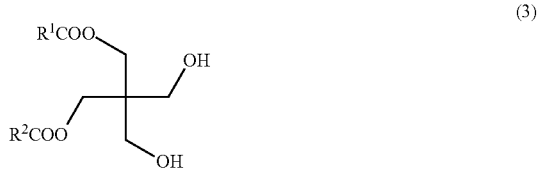

and monoesters of pentaerythritol and fatty acids, represented by the following formula (4).

In the formulae, $R^1$-$R^4$ each represent a chain hydrocarbon.

The fatty acids composing the esters of pentaerythritol and fatty acids ($R^1COOH$, $R^2COOH$, $R^3COOH$, and $R^4COOH$) are not particularly restricted as long as the pentaerythritol and fatty acid esters satisfy the conditions for the IOB, melting point and water solubility, and for example, there may be mentioned saturated fatty acids, such as $C_2$-$C_{30}$ saturated fatty acids, including acetic acid ($C_2$) ($C_2$ representing the number of carbons, corresponding to the number of carbons of each of $R^1C$, $R^2C$, $R^3C$ or $R^4C$, same hereunder), propanoic acid ($C_3$), butanoic acid ($C_4$) and isomers thereof such as 2-methylpropanoic acid ($C_4$), pentanoic acid ($C_5$) and isomers thereof such as 2-methylbutanoic acid ($C_5$) and 2,2-dimethylpropanoic acid ($C_5$), hexanoic acid ($C_6$), heptanoic acid ($C_7$), octanoic acid ($C_8$) and isomers thereof, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$) and triacontanoic acid ($C_{30}$), as well as isomers of the foregoing (excluding those mentioned above).

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, in order to lower the IOB and result in greater hydrophobicity, the ester of pentaerythritol and a fatty acid is preferably a diester, triester or tetraester, more preferably a triester or tetraester, and even more preferably a tetraester.

In a tetraester of pentaerythritol and a fatty acid, the IOB is 0.60 if the total number of carbons of the fatty acid composing the tetraester of the pentaerythritol and fatty acid, i.e., the total number of carbons of the $R^1C$, $R^2C$, $R^3C$ and $R^4C$ portions in formula (1), is 15. Thus, when the total number of carbons of the fatty acid composing the tetraester of the pentaerythritol and fatty acid is approximately 15 or greater, the IOB satisfies the condition of being within about 0.00 to 0.60.

Examples of tetraesters of pentaerythritol and fatty acids include tetraesters of pentaerythritol with hexanoic acid ($C_6$), heptanoic acid ($C_7$), octanoic acid ($C_8$) such as 2-ethylhexanoic acid ($C_8$), nonanoic acid ($C_9$), decanoic acid ($C_{10}$) and/or dodecanoic acid ($C_{12}$).

In a triester of pentaerythritol and a fatty acid, the IOB is 0.58 if the total number of carbons of the fatty acid composing the triester of the pentaerythritol and fatty acid, i.e., the total number of carbons of the $R^1C$, $R^2C$ and $R^3C$ portions in formula (2), is 19. Thus, when the total number of carbons of the fatty acid composing the triester of the pentaerythritol and fatty acid is approximately 19 or greater, the IOB satisfies the condition of being within about 0.00 to 0.60.

In a diester of pentaerythritol and a fatty acid, the IOB is 0.59 if the total number of carbons of the fatty acid composing the diester of the pentaerythritol and fatty acid, i.e., the total number of carbons of the $R^1C$ or $R^2C$ portion in formula (3), is 22. Thus, when the total number of carbons of the fatty acid composing the diester of the pentaerythritol and fatty acid is approximately 22 or greater, the IOB satisfies the condition of being within about 0.00 to 0.60.

In a monoester of pentaerythritol and a fatty acid, the IOB is 0.60 if the total number of carbons of the fatty acid composing the monoester of the pentaerythritol and fatty acid, i.e., the total number of carbons of the $R^1C$ portion in formula (4), is 25. Thus, when the number of carbons of the fatty acid composing the monoester of the pentaerythritol and fatty acid is approximately 25 or greater, the IOB satisfies the condition of being within about 0.00 to 0.60.

The effects of double bonds, triple bonds, iso-branches and tert-branches are not considered in this calculation.

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

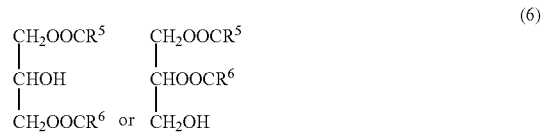

and monoesters of glycerin and fatty acids, represented by the following formula (7):

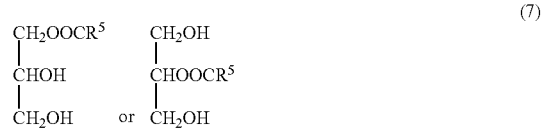

wherein $R^5$-$R^7$ each represent a chain hydrocarbon.

The fatty acid composing the ester of glycerin and a fatty acid ($R^5COOH$, $R^6COOH$ and $R^7COOH$) is not particularly restricted so long as the ester of glycerin and a fatty acid satisfies the conditions for the IOB, melting point and water solubility, and for example, there may be mentioned that the fatty acids mentioned for the "($a_1$) Ester of chain hydrocarbon tetraol and at least one fatty acids", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, in order to lower the IOB and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

In order to obtain a melting point of no higher than about 45° C., preferred triesters of glycerin and fatty acids are those with no more than about 40 as the total number of carbons of the fatty acid composing the triester of glycerin and the fatty acid, i.e., the total number of carbons of the $R^5C$, $R^6C$ and $R^7C$ portions in formula (5).

In a triester of glycerin and a fatty acid, the IOB value is 0.60 when the total number of carbons of the fatty acid composing the triester of glycerin and the fatty acid, i.e., the total number of carbons of the $R^5C$, $R^6C$ and $R^7C$ portions in formula (5), is 12. Thus, when the total number of carbons of the fatty acid comprising the triester of the glycerin and fatty acid is approximately 12 or greater, the IOB satisfies the condition of being within about 0.00 to 0.60.

Triesters of glycerin and fatty acids, being aliphatic and therefore potential constituent components of the human body are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

In a diester of glycerin and a fatty acid, the IOB is 0.58 if the total number of carbons of the fatty acid composing the diester of the glycerin and fatty acid, i.e., the total number of carbons of the $R^5C$ and $R^6C$ portions in formula (6), is 16. Thus, when the total number of carbons of the fatty acid composing the diester of the glycerin and fatty acid is approximately 16 or greater, the IOB satisfies the condition of being about 0.00 to 0.60.

Monoesters of glycerin and fatty acids are also known as monoglycerides, and examples include glycerin and icosanoic acid ($C_{20}$) monoester, and glycerin and docosanoic acid ($C_{22}$) monoester.

In a monoester of glycerin and a fatty acid, the IOB is 0.59 if the number of carbons of the fatty acid composing the monoester of the glycerin and fatty acid, i.e., the number of carbons of the $R^5C$ portion in formula (7), is 19. Thus, when the number of carbons of the fatty acid composing the monoester of the glycerin and fatty acid is approximately 19 or greater, the IOB satisfies the condition of being about 0.00 to 0.60.

[($a_3$) Ester of Chain Hydrocarbon Diol and at Least One Fatty Acid]

Examples of an ester of a chain hydrocarbon diol and at least one fatty acids include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

$$R^8COOC_kH_{2k}OCOR^9 \tag{8}$$

wherein k represents an integer of 2-6, and $R^8$ and $R^9$ each represent a chain hydrocarbon, and monoesters of $C_2$-$C_6$ glycols and fatty acids, represented by the following formula (9):

$$R^8COOC_kH_{2k}OH \tag{9}$$

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the IOB, melting point and water solubility, and for example, there may be mentioned that the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

In a diester of butylene glycol (k=4) and a fatty acid represented by formula (8), IOB is 0.60 when the total number of carbons of the $R^8C$ and $R^9C$ portions is 6. Thus, when the total number of carbon atoms in a diester of butylene glycol (k=4) and a fatty acid represented by formula (8) is approximately 6 or greater, the IOB satisfies the condition of being about 0.00-0.60. In a monoester of ethylene glycol (k=2) and a fatty acid represented by formula (9), IOB is 0.57 when the number of carbons of the $R^8C$ portion is 12. Thus, when the total number of carbon atoms in the fatty acid composing a monoester of ethylene glycol (k=2) and a fatty acid represented by formula (9) is approximately 12 or greater, the IOB satisfies the condition of being about 0.00-0.60.

Considering the potential for degradation by oxidation and the like, the ester of the $C_2$-$C_6$ glycol and fatty acid is preferably a $C_2$-$C_6$ glycol and fatty acid ester, which is derived from a saturated fatty acid, i.e., an ester of a $C_2$-$C_6$ glycol and a saturated fatty acid.

Also, in order to lower the IOB and result in greater hydrophobicity, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, in order to lower the IOB and obtain in greater hydrophobicity, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting Hydrogens on the Chain Hydrocarbon Moiety and (B2) a Compound Having a Chain Hydrocarbon Moiety and 1 Hydroxyl Group Substituting a Hydrogen on the Chain Hydrocarbon Moiety]

The (B) ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety (hereunder also referred to as "compound (B)") includes ethers of a compound with 4, 3 or 2 hydroxyl groups and a compound with 1 hydroxyl group, and it is not necessary for all of the hydroxyl groups to be etherified as long as the IOB, melting point and water solubility are within the aforementioned ranges.

Examples of (B1) a compound having a chain hydrocarbon moiety and 2-4 hydroxyl groups substituting hydrogens on the chain hydrocarbon moiety (hereunder also referred to as "compound (B1)") include those mentioned for "compound (A1)",)" as compound (A1), such as pentaerythritol, glycerin and glycol.

Examples of (B2) a compound having a chain hydrocarbon moiety and 1 hydroxyl group substituting a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and isomers thereof, including isopropyl alcohol ($C_3$), butyl alcohol ($C_4$) and isomers thereof, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and isomers thereof, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C=C double bond, such as oleyl alcohol, and for example, these are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohols, such as monoethers and diethers, and preferably diethers.

Examples of an ether of a chain hydrocarbon tetraol and at least one aliphatic monohydric alcohols include tetraethers, triethers, diethers and monoethers of pentaerythritol and aliphatic monohydric alcohols, represented by the following formulae (10)-(13):

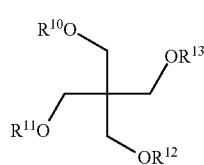

(10)

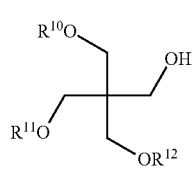

(11)

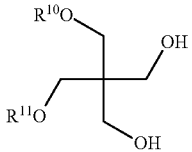

(12)

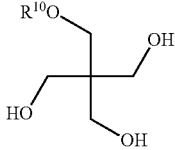

(13)

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulae (14)-(16):

(14)

(15)

(16)

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

(17)

wherein n is an integer of 2-6, and $R^{17}$ and $R^{18}$ are each a chain hydrocarbon,
and monoethers of $C_2$-$C_6$ glycols and aliphatic monohydric alcohols, represented by the following formula (18):

(18)

wherein n is an integer of 2-6, and $R^{17}$ is a chain hydrocarbon.

In the tetraether of pentaerythritol and an aliphatic monohydric alcohol, the IOB is 0.44 when the total number of carbon atoms of the aliphatic monohydric alcohol composing the tetraether of pentaerythritol and the aliphatic monohydric alcohol, i.e., the total number of carbon atoms of the $R^{10}$, $R^{11}$, $R^{12}$ and $R^{13}$ portions in formula (10), is 4. Thus, when the total number of carbon atoms of the aliphatic monohydric alcohol composing a tetraether of pentaerythritol and an aliphatic monohydric alcohol is approximately 4 or greater, the IOB value satisfies the condition of being within about 0.00 to 0.60.

In the triether of pentaerythritol and an aliphatic monohydric alcohol, the IOB is 0.57 when the total number of carbon atoms of the aliphatic monohydric alcohol composing the triether of pentaerythritol and the aliphatic monohydric alcohol, i.e., the total number of carbon atoms of the $R^{10}$, $R^{11}$ and $R^{12}$ portions in formula (11), is 9. Thus, when the total number of carbon atoms of the aliphatic monohydric alcohol composing a triether of pentaerythritol and an aliphatic monohydric alcohol is approximately 9 or greater, the IOB value satisfies the condition of being within about 0.00 to 0.60.

In the diether of pentaerythritol and an aliphatic monohydric alcohol, the IOB is 0.60 when the total number of carbon atoms of the aliphatic monohydric alcohol composing the diether of pentaerythritol and the aliphatic monohydric alcohol, i.e., the total number of carbon atoms of the $R^{10}$ and $R^{11}$ portions in formula (12), is 15. Thus, when the total number of carbon atoms of the aliphatic monohydric alcohol composing a diether of pentaerythritol and an aliphatic monohydric alcohol is approximately 15 or greater, the IOB value satisfies the condition of being within about 0.00 to 0.60.

In the monoether of pentaerythritol and an aliphatic monohydric alcohol, the IOB is 0.59 when the number of carbon atoms of the aliphatic monohydric alcohol composing the monoether of pentaerythritol and the aliphatic monohydric alcohol, i.e., the number of carbon atoms of the $R^{10}$ portion in formula (13), is 22. Thus, when the number of carbon atoms of the aliphatic monohydric alcohol comprising a monoether of pentaerythritol and an aliphatic monohydric alcohol is approximately 22 or greater, the IOB value satisfies the condition of being within about 0.00 to 0.60.

In the triether of glycerin and an aliphatic monohydric alcohol, the IOB is 0.50 when the total number of carbon atoms of the aliphatic monohydric alcohol composing the triether of glycerin and the aliphatic monohydric alcohol, i.e., the total number of carbon atoms of the $R^{14}$, $R^{15}$ and $R^{16}$ portions in formula (14), is 3. Thus, when the total number of carbon atoms of the aliphatic monohydric alcohol comprising a triether of glycerin and an aliphatic monohydric alcohol is approximately 3 or greater, the IOB value satisfies the condition of being within about 0.00 to 0.60.

In the diether of glycerin and an aliphatic monohydric alcohol, the IOB is 0.58 when the total number of carbon atoms of the aliphatic monohydric alcohol composing the diether of glycerin and the aliphatic monohydric alcohol, i.e., the total number of carbon atoms of the $R^{14}$ and $R^{15}$ portions in formula (15), is 9. Thus, when the total number of carbon atoms of the aliphatic monohydric alcohol comprising a diether of glycerin and an aliphatic monohydric alcohol is approximately 9 or greater, the IOB value satisfies the condition of being within about 0.00 to 0.60.

In the monoether of glycerin and an aliphatic monohydric alcohol, the IOB is 0.58 when the number of carbon atoms of the aliphatic monohydric alcohol composing the monoether of glycerin and the aliphatic monohydric alcohol, i.e., the number of carbon atoms of the $R^{14}$ portion in formula (16), is 16. Thus, when the number of carbon atoms of the aliphatic monohydric alcohol comprising a monoether of glycerin and an aliphatic monohydric alcohol is approximately 16 or greater, the IOB value satisfies the condition of being within about 0.00 to 0.60.

In a diether of butylene glycol (n=4) and aliphatic monohydric alcohol represented by formula (17), the IOB is 0.33 when the total number of carbon atoms of the $R^{17}$ and $R^{18}$ portions is 2. Thus, when the number of carbon atoms of the aliphatic monohydric alcohol comprising a diether of butylene glycol (n=4) and an aliphatic monohydric alcohol represented by formula (17) is approximately 2 or greater, the IOB value satisfies the condition of being within about 0.00 to 0.60. Also, in a monoether of ethylene glycol (n=2) and aliphatic monohydric alcohol represented by formula (18), the IOB is 0.60 when the number of carbon atoms of the $R^{17}$ portion is 8. Thus, when the number of carbon atoms of the aliphatic monohydric alcohol in a monoether of ethylene glycol (n=2) and an aliphatic monohydric alcohol represented by formula (18) is approximately 8 or greater, the IOB value satisfies the condition of being within about 0.00 to 0.60.

Compound (B) may be produced by dehydrating condensation of a compound with 2-4 hydroxyl groups (B1) and a compound with 1 hydroxyl group, such as an aliphatic monohydric alcohol (B2), in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting Hydrogens on the Chain Hydrocarbon Moiety and (C2) a Compound Having a Chain Hydrocarbon Moiety and 1 Hydroxyl Group Substituting a Hydrogen on the Chain Hydrocarbon Moiety]

The (C) ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety (hereunder also referred to as "compound (C)") includes esters of a compound with 4, 3 or 2 carboxyl groups and a compound with 1 hydroxyl group, and it is not necessary for all of the carboxyl groups to be esterified so long as the IOB, melting point and water solubility are within the aforementioned ranges.

Examples of (C1) a carboxylic acid, hydroxy acid, alkoxy acid or oxoacid comprising a chain hydrocarbon moiety and 2-4 carboxyl groups substituting hydrogens on the chain hydrocarbon moiety (hereunder also referred to as "compound (C1)") include chain hydrocarbons hydrocarbon carboxylic acids with 2-4 carboxyl groups, such as chain hydrocarbon dicarboxylic acids including alkanedicarboxylic acids such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, including alkoxy acids with 2-4 carboxyl groups such as malic acid, tartaric acid, citric acid and isocitric acid, including chain hydrocarbon alkoxy acids with 2-4 carboxyl groups, such as O-acetylcitric acid, and chain hydrocarbon oxoacids with 2-4 carboxyl groups.

Compounds (C2) having a chain hydrocarbon moiety and 1 hydroxyl group substituting a hydrogen on the chain hydrocarbon moiety include those mentioned for "compound (B)", such as aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or $(c_3)$ an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted in a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted in-between a C—C single bond of the chain hydrocarbon moiety (hereunder also referred to as "compound (D)") may be $(d_1)$ an ether of an aliphatic monohydric alcohol and an aliphatic monohydric alcohol, $(d_2)$ a dialkyl ketone, $(d_3)$ an ester of a fatty acid and an aliphatic monohydric alcohol, or $(d_4)$ a dialkyl carbonate.

[$(d_1)$ Ether of an Aliphatic Monohydric Alcohol and an Aliphatic Monohydric Alcohol]

Ethers of aliphatic monohydric alcohols and aliphatic monohydric alcohols include compounds having the following formula (19):

$$R^{19}OR^{20} \quad (19)$$

wherein $R^{19}$ and $R^{20}$ each represent a chain hydrocarbon.

The aliphatic monohydric alcohol composing the ether (corresponding to $R^{19}OH$ and $R^{20}OH$ in formula (19)) is not particularly restricted so long as the ether satisfies the conditions for the IOB, melting point and water solubility, and for example, it may be one of the aliphatic monohydric alcohols mentioned for "compound (B)".

In an ether of an aliphatic monohydric alcohol and an aliphatic monohydric alcohol, the IOB is 0.50 when the total number of carbon atoms of the aliphatic monohydric alcohols composing the ether, i.e., the total number of carbons of the $R^{10}$ and $R^{20}$ portions in formula (19), is 2, and therefore when the total number of carbons of the aliphatic monohydric alcohols comprising the ether is about 2 or greater, this condition for the IOB is satisfied. However, when the total number of carbons of the aliphatic monohydric alcohols comprising the ether is about 6, the water solubility is as high as about 2 g, which is problematic from the viewpoint of vapor pressure as well. In order to satisfy the condition of a water solubility of about 0.00-0.05 g, the total number of carbons of the aliphatic monohydric alcohols comprising the ether is preferably about 8 or greater.

[$(d_2)$ Dialkyl Ketone]

The dialkyl ketone may be a compound of the following formula (20):

$$R^{21}COR^{22} \quad (20)$$

wherein $R^{21}$ and $R^{22}$ are each an alkyl group.

In a dialkyl ketone, the IOB is 0.54 when the total number of carbon atoms of $R^{21}$ and $R^{22}$ is 5, and therefore this condition for the IOB is satisfied if the total number of carbons is about 5 or greater. However, when the total number of carbons of dialkyl ketone is about 5, the water solubility is as high as about 2 g. Therefore, in order to satisfy the condition of a water solubility of about 0.00-0.05 g, the total number of carbons of dialkyl ketone is preferably about 8 or greater. In consideration of vapor pressure, the number of carbon atoms of dialkyl ketone is preferably about 10 or greater and more preferably about 12 or greater.

If the total number of carbon atoms of alkyl ketone is about 8, such as in 5-nonanone, for example, the melting point is approximately −50° C. and the vapor pressure is about 230 Pa at 20° C.

The dialkyl ketone may be a commercially available product, or it may be obtained by a known method, such as by oxidation of a secondary alcohol with chromic acid or the like.

[$(d_3)$ Ester of a Fatty Acid and an Aliphatic Monohydric Alcohol]

Examples of esters of fatty acids and aliphatic monohydric alcohols include compounds having the following formula (21):

$$R^{23}COOR^{24} \quad (21)$$

wherein $R^{23}$ and $R^{24}$ each represent a chain hydrocarbon.

Examples of fatty acids composing these esters (corresponding to $R^{23}COOH$ in formula (21)) include the fatty acids mentioned for the "$(a_1)$ an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol composing the ester (corresponding to $R^{24}OH$ in formula (21)) may be one of the aliphatic monohydric alcohols mentioned for "compound (B)".

In an ester of such a fatty acid and aliphatic monohydric alcohol, the IOB is 0.60 when the total number of carbon atoms of the fatty acid and aliphatic monohydric alcohol, i.e., the total number of carbon atoms of the $R^{23}C$ and $R^{24}$ portion in formula (21), is 5, and therefore this condition for the IOB is satisfied when the total number of carbon atoms of the $R^{23}C$ and $R^{24}$ portion is about 5 or greater. However, with butyl acetate in which the total number of carbon atoms is 6, the vapor pressure is high at greater than 2000 Pa. In consideration of vapor pressure, therefore, the total number of carbon atoms is preferably about 12 or greater. If the total number of carbon atoms is about 11 or greater, it will be possible to satisfy the condition of a water solubility of about 0.00-0.05 g.

Examples of esters of such fatty acids and aliphatic monohydric alcohols include esters of dodecanoic acid $(C_{12})$ and dodecyl alcohol $(C_{12})$ and esters of tetradecanoic acid $(C_{14})$ and dodecyl alcohol $(C_{12})$, and examples of commercial products of esters of such fatty acids and aliphatic monohydric alcohols include ELECTOL WE20 and ELECTOL WE40 (both products of NOF Corp.).

[$(d_4)$ Dialkyl Carbonate]

The dialkyl carbonate may be a compound of the following formula (22):

$$R^{25}OC(=O)OR^{26} \quad (22)$$

wherein $R^{25}$ and $R^{26}$ are each an alkyl group.

In a dialkyl carbonate, the IOB is 0.57 when the total number of carbon atoms of $R^{25}$ and $R^{26}$ is 6, and therefore this condition for the IOB is satisfied if the total number of carbons of $R^{25}$ and $R^{26}$ is about 6 or greater.

In consideration of water solubility, the total number of carbon atoms of $R^{25}$ and $R^{26}$ is preferably about 7 or greater and more preferably about 9 or greater.

The dialkyl carbonate may be a commercially available product, or it may be synthesized by reaction between phosgene and an alcohol, reaction between formic chloride and an alcohol or alcoholate, or reaction between silver carbonate and an alkyl iodide.

[(E) Polyoxy $C_2$-$C_6$ Alkylene Glycol, or Alkyl Ester or Alkyl Ether Thereof]

The (E) polyoxy $C_2$-$C_6$ alkylene glycol, or alkyl ester or alkyl ether thereof (hereunder also referred to as "compound (E)") may be ($e_1$) a polyoxy $C_2$-$C_6$ alkylene glycol, ($e_2$) an ester of a polyoxy $C_2$-$C_6$ alkylene glycol and at least one fatty acid, ($e_3$) an ether of a polyoxy $C_2$-$C_6$ alkylene glycol and at least one aliphatic monohydric alcohol, ($e_4$) an ester of polyoxy $C_2$-$C_6$ alkylene glycol and a chain hydrocarbon tetracarboxylic acid, chain hydrocarbon tricarboxylic acid or chain hydrocarbon dicarboxylic acid, or ($e_5$) an ether of polyoxy $C_2$-$C_6$ alkylene glycol and chain hydrocarbon tetraol, chain hydrocarbon triol or chain hydrocarbon diol. These will now be explained.

[($e_1$) Polyoxy $C_2$-$C_6$ Alkylene Glycol]

The polyoxy $C_2$-$C_6$ alkylene glycol is i) a homopolymer having one backbone selected from the group consisting of polyoxy $C_2$-$C_6$ alkylene backbones, i.e., oxyethylene backbone, oxypropylene backbone, oxybutylene backbone, oxypentylene backbone and oxyhexylene backbone, and having hydroxy groups at both ends, ii) a block copolymer having a backbone of 2 or more selected from among the aforementioned group and having hydroxy groups at both ends, or iii) a random copolymer having a backbone of two or more selected from among the aforementioned group and having hydroxy groups at both ends.

The polyoxy $C_2$-$C_6$ alkylene backbone is preferably an oxypropylene backbone, oxybutylene backbone, oxypentylene backbone or oxyhexylene backbone and more preferably an oxybutylene backbone, oxypentylene backbone or oxyhexylene backbone, from the viewpoint of lowering the IOB of the polyoxy $C_2$-$C_6$ alkylene glycol.

When polyoxy $C_2$-$C_6$ alkylene glycol is a homopolymer, the poly $C_{3-6}$ alkylene glycol is represented by the following formula (23):

$$HO\text{---}(C_mH_{2m}O)_n\text{---}H \tag{23}$$

wherein m is an integer of 3-6.

The present inventors have confirmed that in polyethylene glycol (corresponding to formula (23) where m=2), when n≥45 (the molecular weight exceeds about 2,000), the condition for IOB of about 0.00 to about 0.60 is satisfied, but the condition for the water solubility is not satisfied even when the molecular weight exceeds 4,000. Therefore, ethylene glycol homopolymer is not included in the ($e_1$) polyoxy $C_2$-$C_6$ alkylene glycol, and ethylene glycol should be included in the ($e_1$) polyoxy $C_2$-$C_6$ alkylene glycol only as a copolymer or random polymer with another glycol.

Thus, homopolymers of formula (23) may include propylene glycol, butylene glycol, pentylene glycol or hexylene glycol homopolymer.

For this reason, m in formula (23) is about 3 to 6 and preferably about 4 to 6, and n is 2 or greater.

The value of n in formula (23) is a value such that the polyoxy $C_2$-$C_6$ alkylene glycol has an IOB of about 0.00-0.60, a melting point of no higher than about 45° C. and a water solubility of no greater than about 0.05 g in 100 g of water at 25° C.

For example, when formula (23) is polypropylene glycol (m=3), the IOB is 0.58 when n=12. Thus, when formula (23) is polypropylene glycol (m=3), the condition for the IOB is satisfied when n is equal to or greater than about 12.

Also, when formula (23) is polybutylene glycol (m=4), the IOB is 0.57 when n=7. Thus, when formula (23) is polybutylene glycol (m=4), the condition for the IOB is satisfied when n is equal to or greater than about 7.

From the viewpoint of IOB, melting point and water solubility, the weight-average molecular weight of the polyoxy $C_2$-$C_6$ alkylene glycol is preferably between about 200 and about 10,000, more preferably between about 250 and about 8,000, and even more preferably in the range of about 250 to about 5,000.

Also from the viewpoint of IOB, melting point and water solubility, the weight-average molecular weight of a poly $C_3$ alkylene glycol, i.e., polypropylene glycol, is preferably between about 1,000 and about 10,000, more preferably between about 3,000 and about 8,000, and even more preferably between about 4,000 and about 5,000. This is because if the weight-average molecular weight is less than about 1,000, the condition for the water solubility will not be satisfied, and a larger weight-average molecular weight will particularly tend to increase the migration rate into the absorbent body and the whiteness of the top sheet.

Examples of commercial products of polyoxy $C_2$-$C_6$ alkylene glycols include UNIOL™ D-1000, D1200, D-2000, D-3000, D-4000, PB-500, PB-700, PB-1000 and PB-2000 (both products of NOF Corp.).

[($e_2$) Ester of Polyoxy $C_2$-$C_6$ Alkylene Glycol and at Least One Fatty Acid]

Esters of such polyoxy $C_2$-$C_6$ alkylene glycols and at least one fatty acid include the polyoxy $C_2$-$C_6$ alkylene glycols mentioned for "($e_1$) Polyoxy $C_2$-$C_6$ alkylene glycol" in which one or both OH ends have been esterified with fatty acids, i.e., monoesters and diesters.

Examples of fatty acids to be esterified in the ester of a polyoxy $C_2$-$C_6$ alkylene glycol and at least one fatty acid include the fatty acids mentioned for the "($a_1$) Esters of chain hydrocarbon tetraols and at least one fatty acid", and specifically these include saturated fatty acids and unsaturated fatty acids, with saturated fatty acids being preferred in consideration of the potential for degradation by oxidation and the like. An example of a commercially available ester of a polyoxy $C_2$-$C_6$ alkylene glycol a fatty acid is WILLBRITE cp9 (product of NOF Corp.).

[($e_3$) Ether of Polyoxy $C_2$-$C_6$ Alkylene Glycol and at Least One Aliphatic Monohydric Alcohol]

Ethers of such polyoxy $C_2$-$C_6$ alkylene glycols and at least one aliphatic monohydric alcohol include the polyoxy $C_2$-$C_6$ alkylene glycols mentioned for "($e_1$) polyoxy $C_2$-$C_6$ alkylene glycol" wherein one or both OH ends have been etherified by an aliphatic monohydric alcohol, i.e., monoethers and diethers.

In an ether of a polyoxy $C_2$-$C_6$ alkylene glycol and at least one aliphatic monohydric alcohol, the aliphatic monohydric alcohol to be etherified may be an aliphatic monohydric alcohol among those mentioned for "compound (B)".

[($e_4$) Ester of Polyoxy $C_2$-$C_6$ Alkylene Glycol and Chain Hydrocarbon Tetracarboxylic Acid, Chain Hydrocarbon Tricarboxylic Acid or Chain Hydrocarbon Dicarboxylic Acid]

The polyoxy $C_2$-$C_6$ alkylene glycol to be esterified for the aforementioned ester of a polyoxy $C_2$-$C_6$ alkylene glycol and a chain hydrocarbon tetracarboxylic acid, chain hydrocarbon tricarboxylic acid or chain hydrocarbon dicarboxylic acid may be any of the polyoxy $C_2$-$C_6$ alkylene glycols mentioned above under "($e_1$) Polyoxy $C_2$-$C_6$ alkylene glycol". Also, the chain hydrocarbon tetracarboxylic acid, chain hydrocarbon tricarboxylic acid or chain hydrocarbon dicarboxylic acid to be esterified may be any of those mentioned above for "compound (C)".

The ester of a polyoxy $C_2$-$C_6$ alkylene glycol and a chain hydrocarbon tetracarboxylic acid, chain hydrocarbon tricarboxylic acid or chain hydrocarbon dicarboxylic acid may be a commercially available product, or it may be produced by polycondensation of a polyoxy $C_2$-$C_6$ alkylene glycol with a chain hydrocarbon tetracarboxylic acid, chain hydrocarbon tricarboxylic acid or chain hydrocarbon dicarboxylic acid under known conditions.

[($e_5$) Ether of Polyoxy $C_2$-$C_6$ Alkylene Glycol and Chain Hydrocarbon Tetraol, Chain Hydrocarbon Triol or Chain Hydrocarbon Diol]

The polyoxy $C_2$-$C_6$ alkylene glycol to be etherified for the aforementioned ether of a polyoxy $C_2$-$C_6$ alkylene glycol and a chain hydrocarbon tetraol, chain hydrocarbon triol or chain hydrocarbon diol may be any of the polyoxy $C_2$-$C_6$ alkylene glycols mentioned above under "($e_1$) Polyoxy $C_2$-$C_6$ alkylene glycol". Also, the chain hydrocarbon tetraol, chain hydrocarbon triol or chain hydrocarbon diol to be etherified may be, for example, pentaerythritol, glycerin or glycol, mentioned above for "compound (A)".

Examples of commercially available ethers of polyoxy $C_2$-$C_6$ alkylene glycols and chain hydrocarbon tetraols, chain hydrocarbon triols and chain hydrocarbon diols include UNILUBE™ 5 TP-300 KB and UNIOL™ TG-3000 and TG-4000 (products of NOF Corp.).

UNILUBE™ 5 TP-300 KB is a compound obtained by polycondensation of 65 mol of propylene glycol and 5 mol of ethylene glycol with 1 mol of pentaerythritol, and it has an IOB of 0.39, a melting point of below 45° C., and a water solubility of less than 0.05 g.

UNIOL™ TG-3000 is a compound obtained by polycondensation of 50 mol of propylene glycol with 1 mol of glycerin, and it has an IOB of 0.42, a melting point of below 45° C., a water solubility of less than 0.05 g, and a weight-average molecular weight of about 3,000.

UNIOL™ TG-4000 is a compound obtained by polycondensation of 70 mol of propylene glycol with 1 mol of glycerin, and it has an IOB of 0.40, a melting point of below 45° C., a water solubility of less than 0.05 g, and a weight-average molecular weight of about 4,000.

The ether of a poly $C_2$-$C_6$ alkylene glycol and a chain hydrocarbon tetraol, chain hydrocarbon triol or chain hydrocarbon diol may also be produced by polycondensation of a polyoxy $C_2$-$C_6$ alkylene glycol with a chain hydrocarbon tetraol, chain hydrocarbon triol or chain hydrocarbon diol under known conditions.

[(F) Chain Hydrocarbon]

The chain hydrocarbon has an inorganic value of 0 and thus an IOB of 0.00, while the water solubility is also approximately 0 g, and therefore if the melting point is no higher than about 45° C., it may be included among the aforementioned blood modifying agents. Examples of such chain hydrocarbons include ($f_1$) chain alkanes, such as linear alkanes and branched alkanes, and linear alkanes generally include those with no more than 22 carbons, in consideration of a melting point of no higher than about 45° C. In consideration of vapor pressure, they generally include those with 13 or more carbons. Branched alkanes generally include those with 22 or more carbons, since their melting points are often lower than linear alkanes, given the same number of carbon atoms.

Examples of commercially available hydrocarbon products include PARLEAM 6 (NOF Corp.).

The blood modifying agent has been found to have at least a function of lowering blood viscosity and surface tension, which will be considered in detail in the examples. Menstrual blood to be absorbed by the absorbent article contains proteins of the endometrial wall, for example, unlike ordinary blood, which act to bind together blood cells, such that the blood cells form a rouleau state. The menstrual blood to be absorbed by the absorbent article therefore tends to have high viscosity, and if the top sheet is a nonwoven fabric of woven fabric, the menstrual blood becomes clogged between the fibers creating a residual sticky feel for the wearer, while the menstrual blood also diffuses on the surface of the top sheet and tends to leak.

Also, in the absorbent article of this disclosure, the blood modifying agent has a melting point of no higher than about 45° C., and therefore, whether liquid or solid at ordinary temperature (25° C.), when it contacts with body fluid at approximately 30-40° C., it liquefies (or is a liquid) and readily dissolves in the body fluid.

Also, the blood modifying agent which has an IOB of about 0.00 to 0.60 has high organicity and readily infiltrates between blood cells, and it therefore stabilizes the blood cells and can prevent formation of a rouleau structure by the blood cells.

Since the blood modifying agent stabilizes blood cells and helps to prevent formation of a rouleau structure by the blood cells, it facilitates absorption of menstrual blood by the absorbent body. For example, with an absorbent article comprising an acrylic super-absorbent polymer, or SAP, absorption of menstrual blood is known to lead to covering of the SAP surface by rouleau-formed blood cells and inhibition of the absorption performance of the SAP, but presumably stabilization of the blood cells allows the absorption performance of the SAP to be exhibited more easily. In addition, the blood modifying agent which has high affinity with erythrocytes protects the erythrocyte membranes, and therefore may minimize destruction of the erythrocytes.

Figure 7:
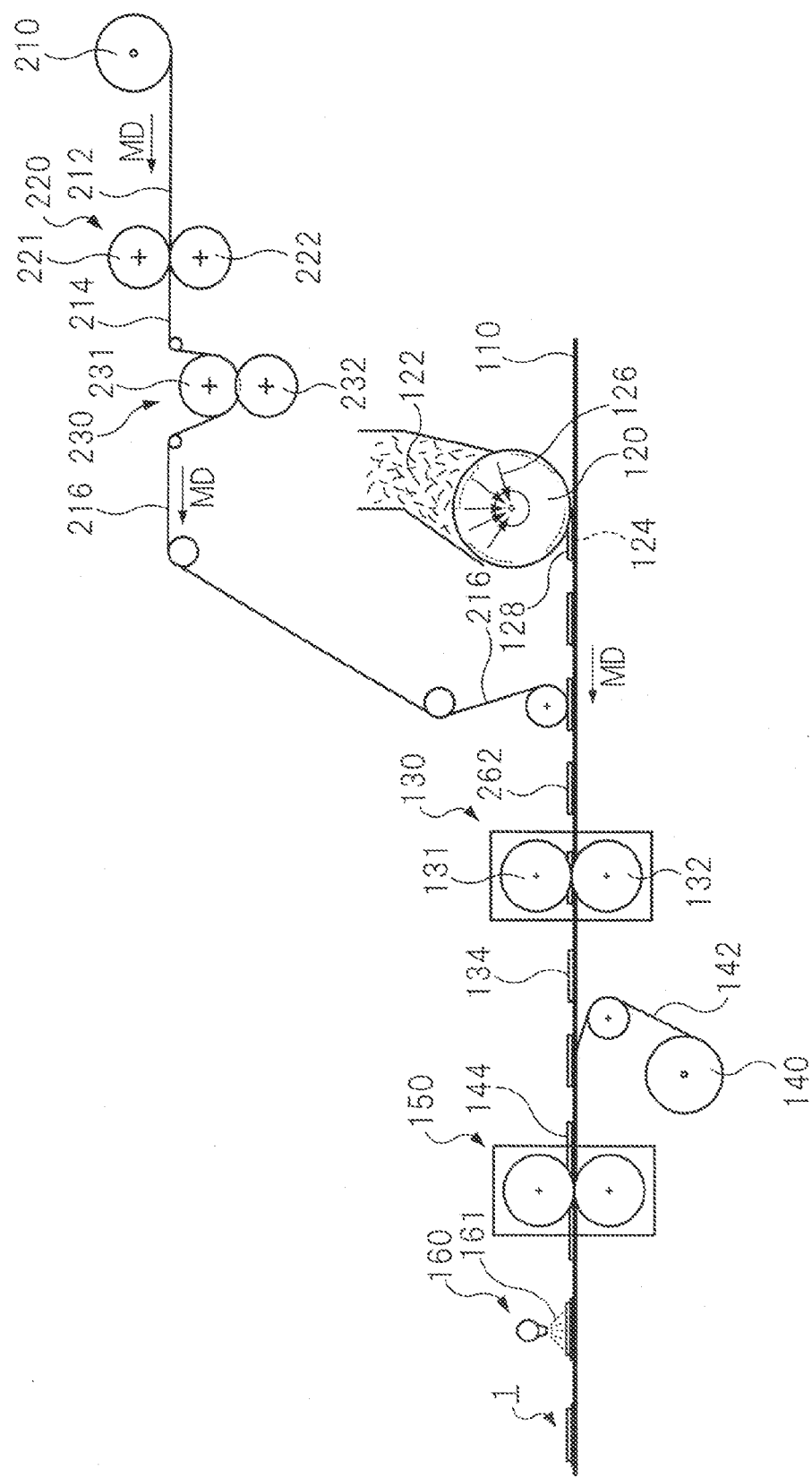
FIG. 7 is a diagram illustrating an embodiment of a method for producing an absorbent article according to an embodiment of the invention.

A method for producing the absorbent article 1 according to an embodiment of the invention will now be explained with reference to FIG. 7. FIG. 7 is an illustration of an absorbent article production apparatus 100 to be used in a method for producing an absorbent article 1 according to an embodiment of the invention. The method for producing the absorbent article 1 comprises a step of forming an absorbent body, a step of preparing a sheet for a top sheet, a step of forming compressed grooves in a layered body, a step of preparing a sheet for a back sheet, a step of cutting continuous sections in the absorbent article, and a step of coating the absorbent article with a blood modifying agent. The sheet for a top sheet, which is to be used in the step of preparing a sheet for a top sheet, is produced by a method for producing a sheet for a top sheet comprising a step of preparing a resin film sheet, a step of forming recesses in the resin film sheet and a step of gear stretching the resin film sheet.

In the step of forming the absorbent body, the absorbent body 128 is formed on a belt 110. Ground pulp 122 is supplied from a ground pulp supply apparatus (not shown), to a pattern drum 120. Recesses 124 are formed around the outer periphery of the pattern drum 120, as a mold into which the ground pulp is to be filled. The interior of the pattern drum 120 is aspirated 126, and the ground pulp 122 supplied to the pattern drum 120 is drawn into the recesses 124 and compressed. The compressed pulp 122 in the recesses 124 is molded into an absorbent body 128. The absorbent body 128 is placed on a belt.

In the step of preparing the sheet for a top sheet, the sheet for a top sheet 216, produced by the method for producing a sheet for a top sheet described below, is placed on the absorbent body 128 and the sheet for a top sheet 216 is bonded to the absorbent body 128.

In the step of forming compressed grooves in the layered body, an embossing apparatus 130 is used to form compressed grooves in the sheet for a top sheet 216 and the layered body 262 of the absorbent body 128. The layered body 262 passes between the upper roll 131 and lower roll 132 of the embossing apparatus 130. Heights (not shown) with shapes corresponding to the compressed grooves 7 of the absorbent article 1 shown in FIG. 1 are provided on the outer peripheral surface of the upper roll 131. The lower roll 132 is a plain roll having a smooth outer peripheral surface. By passing the layered body 262 between the upper roll 131 and lower roll 132 of the embossing apparatus 130, the sections corresponding to the compressed grooves 7 of the absorbent article 1 shown in FIG. 1 become compressed in the thickness direction of the layered body 262, forming compressed grooves in the layered body 262.

In the step of preparing the sheet for the back sheet, the sheet 142 for a back sheet supplied from a back sheet roll 140 is coated with an adhesive using a coating applicator (not shown), and it is then bonded with the surface of the layered body 134 on which the compressed grooves have been formed, on the side opposite the side for the sheet for a top sheet, to form continuous sections 144 in the absorbent article.

In the step of cutting the continuous sections of the absorbent article, a cutter 150 is used for cutting of the continuous sections 144 of the absorbent article into the shape of the absorbent article, producing an absorbent article.

In the step of coating the absorbent article with a blood modifying agent, a modifying agent-coating spray 160 is used to coat the blood modifying agent 161 onto the center region of the absorbent article, forming a blood modifying agent layer on the surface of the top sheet.

The blood modifying agent 161 to be coated on the center region of the absorbent article may be coated at least on the section corresponding to the body fluid excretion hole of the wearer. For example, the blood modifying agent may be coated on a region having a length in the lengthwise direction of preferably 50 mm or greater and more preferably 10 mm or greater and a length in the widthwise direction of preferably 10 mm or greater and more preferably 30 mm or greater, centered around the center of the absorbent article.

The blood modifying agent was coated after the step of cutting the continuous sections of the absorbent article, but the blood modifying agent may instead be coated in the step of producing the sheet for a top sheet described hereunder. In order to prevent the coated blood modifying agent from falling from the absorbent article during production of the absorbent article, it is preferred to coat the blood modifying agent onto the absorbent article at a stage downstream from the absorbent article production step, such as immediately before packaging the absorbent article.

The method for producing the absorbent article 1 may further comprise a step of forming a pressure-sensitive adhesive section on the continuous sections 144 of the absorbent article, and a step of forming a seal section on the continuous sections 144 of the absorbent article.

A method for producing a sheet for a top sheet will now be described.

In the step of preparing the resin film sheet, as shown in FIG. 7, the resin film sheet 212 supplied from a resin film sheet roll 210 is supplied to a recess-forming roll 220.

Figure 9:
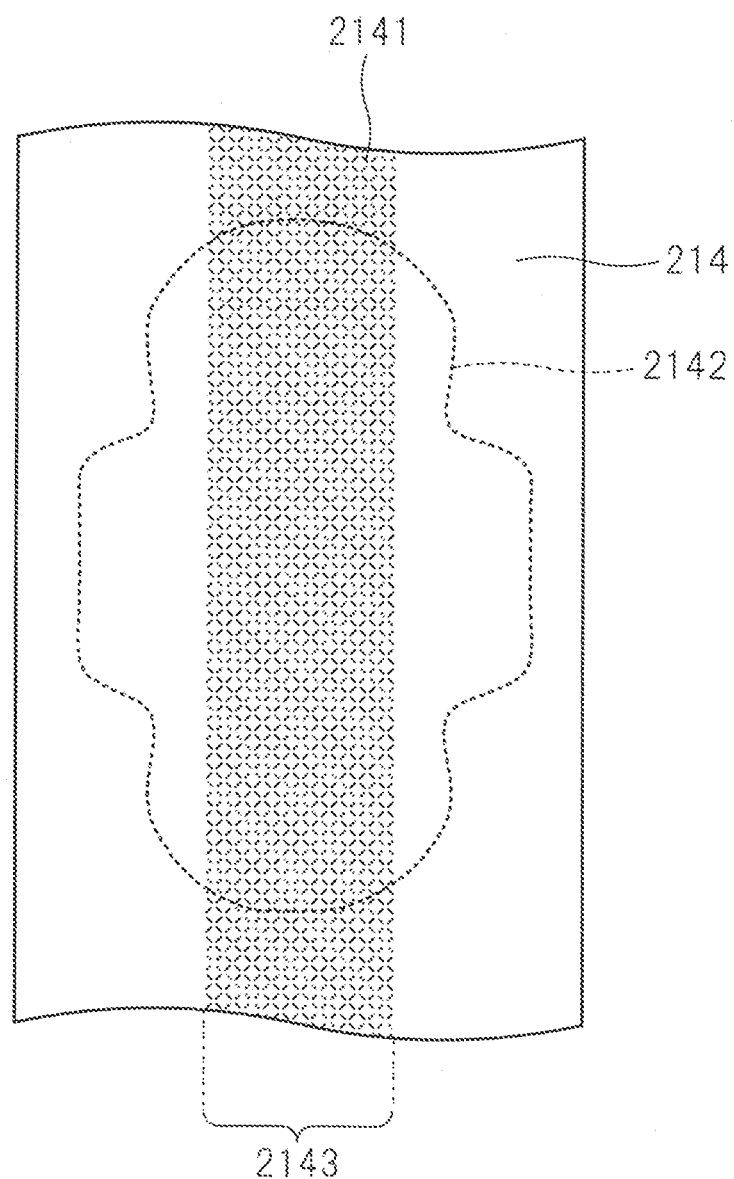
FIG. 9 is a diagram illustrating the region in which recesses are formed by a recess-forming roll in a sheet for a top sheet.

In the step of forming recesses in the resin film sheet, the resin film sheet 212 is passed through recess-forming rolls 220 to produce a resin film sheet 214 having recesses 2141 formed therein (see FIG. 9). The recess-forming roll 220 comprises a roulette roll 221 and a preheated roll 222 with a smooth surface.

FIGS. 8(*a*) and (*b*) show an example of the roulette roll 221. FIG. 8(*a*) shows the entire roulette roll 221, and FIG. 8(*b*) is a magnified view of section 223 having concavoconvexities on the outer peripheral surface of the roulette roll 221. FIG. 8(*c*) shows an example of the preheated roll 222 which has a smooth surface. Lattice-like heights 224 are formed on the surface 223 of the roulette roll 221. As a result, rhomboid recesses 225 are formed in the surface of the roulette roll 221. The shapes of the recesses 225 of the roulette roll 221 are not limited to being rhomboid, and may instead be square, rectangular, parallelogram-shaped, trapezoid, triangular, hexagonal, or the like.

The center line spacing between the heights 224 arranged parallel on the lattice-like heights 224, i.e. the pitch of the lattice-like heights 224, is preferably at least 0.2 mm and no greater than 10 mm and more preferably at least 0.4 mm and no greater than 2 mm. If the pitch of the lattice-like heights 224 is less than 0.2 mm or greater than 10 mm, recesses may not form in the resin film. The widths of the lattice-like heights 224 are preferably at least 0.01 mm and no greater than 1 mm, and more preferably at least 0.03 mm and no greater than 0.1. The lengths of the sides of the rhomboid recesses 225 are preferably at least 0.1 mm and no greater than 5 mm, and more preferably at least 0.2 mm and no greater than 1 mm. If the widths of the lattice-like heights 224 are less than 0.01 mm or greater than 1 mm, or if the lengths of the sides of the rhomboid recesses 225 are less than 0.1 mm or greater than 5 mm, recesses may not form in the resin film.

The preheated roll 222 with a smooth surface is kept at a temperature between 70° C. and 100° C., and it heats the supplied resin film sheet 212. This softens the resin film sheet 212 and facilitates formation.

When the resin film sheet 212 passes between the roulette roll 221 and the roll 222 with a smooth surface, the resin film sheet 212 receives strong pressure in the thickness direction at the sections in contact with the lattice-like heights 224. This causes thin recesses 2141 to form in the resin film sheet 214, as shown in FIG. 9. The recesses 2141 formed in the resin film sheet 212 are actually smaller than shown in FIG. 9, and the number of recesses 2141 per unit area is much greater than shown in FIG. 9. The recesses 2141 are formed only in the region 2143 of the resin film sheet 214 corresponding to the region 12 of the absorbent article 1 in which the absorbent body 4 is provided (see FIG. 1). The region of the resin film sheet 214 corresponding to the absorbent article 1 is the region indicated by the dotted line denoted as 2142.

In the step of gear stretching the resin film sheet, the first protrusions, second protrusions and bottom sections of the top sheet 2 are formed in the resin film sheet 214 by passing the recess-formed resin film sheet 214 through the stretching gear roll 230 shown in FIG. 7. Numeral 216 denotes the resin film sheet in which the first protrusions, second protrusions and bottom sections have been formed.

The stretching gear roll 230 comprises an upper roll 231 and a lower roll 232. FIG. 10(*a*) is a diagram illustrating the upper roll 231 of the stretching gear roll 230, FIG. 10(*b*) is a diagram illustrating the gear teeth 233 situated on the peripheral surface of the upper roll 231, and FIG. 10(*c*) is a cross-sectional view of FIG. 10(*b*) along line B-B. The gear teeth 233 extend in a discontinuous manner in the circumferential direction of the upper roll 231. That is, the gear teeth 233 extending in the circumferential direction of the upper roll 231 are interrupted at multiple locations along them. The locations 234 where the gear teeth 233 are interrupted result in formation of second protrusions in the resin film sheet 214.

The widths of the gear teeth 233 are between 0.3 mm and 0.5 mm, for example, and the distance between the centers of the adjacent gear teeth 233 are between 1.0 mm and 1.2 mm, for example.

FIG. 11(a) is a diagram illustrating the lower roll 232 of the stretching gear roll 230, FIG. 11(b) is a diagram illustrating the gear teeth 235 situated on the peripheral surface of the lower roll 232, and FIG. 11(c) is a cross-sectional view of FIG. 11(b) along line C-C. The gear teeth 235 extend in the circumferential direction of the lower roll 232. The lower roll 232, unlike the upper roll 231, is not interrupted at multiple locations along it. The widths of the gear teeth 235 may be equal to the widths of the gear teeth 233 of the upper roll 231, for example, and the distance between the centers of adjacent gear teeth 235 may be equal to the distance between the centers of the gear teeth 233 of the upper roll 231, for example.

The length of the upper roll 231 in the radial direction at the section where the gear teeth 233 of the upper roll 231 engage with the gear teeth 235 of the lower roll 232, i.e., the mesh depth, is 1.25 mm, for example. The gaps between the gear teeth 233 of the upper roll 231 and the gear teeth 235 of the lower roll 232, when the gear teeth 233 of the upper roll 231 and the gear teeth 235 of the lower roll 232 have been meshed, are between 0.25 mm and 0.45 mm, for example.

As shown in FIG. 7, when the resin film sheet 214 passes through the stretching gear roll 230, the resin film 214 is bent into a roughly undulating form, forming the first protrusions 21 and second protrusions 22 of the top sheet 2 in the resin film 214. Openings 25 of the top sheet 2 (see FIG. 4) are also formed in the region 2143 of the resin film sheet 214 in which the recesses 2141 have been formed (see FIG. 9).

Figure 12:
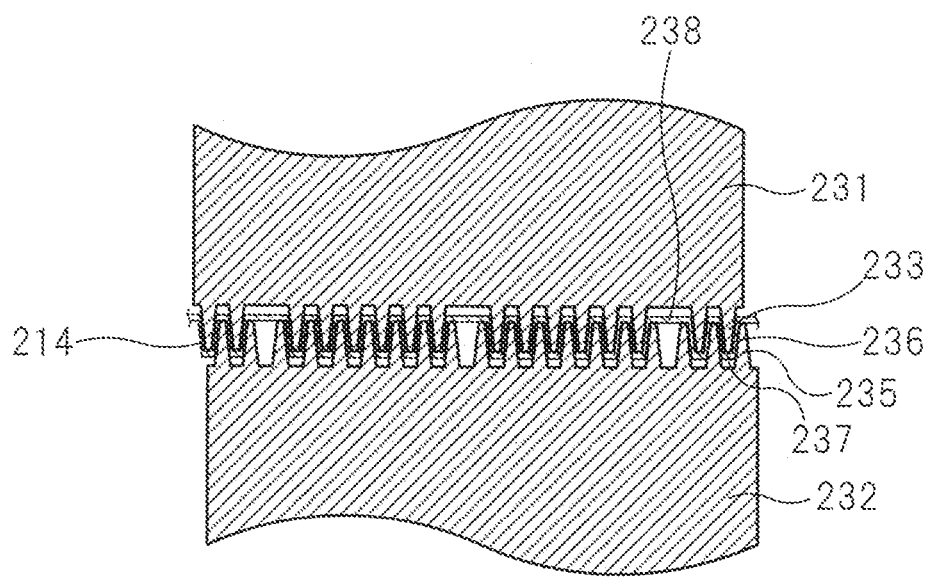
FIG. 12 is an illustration of a sheet for a top sheet to be stretched by a stretching gear roll.

The principle by which openings are formed in the resin film sheet 214 after the resin film sheet 214 has passed through the stretching gear roll 230 will now be explained with reference to FIG. 12. The explanation of this principle is not intended to limit the scope of the invention.

The resin film sheet 214 is stretched to a large degree at the sections 236 where the gear teeth 233 of the upper roll 231 and the gear teeth 235 of the lower roll 232 are meshed. Since the resin film sheet 214 is thinner at the sections in which the recesses 2141 (see FIG. 9) have been formed in the recess-forming step, and they are also the sections that have been damaged by the lattice-like heights 224 of the roulette roll 221, their strength is weak and the recesses 2141 of the resin film sheet 214 tear when subjected to stretching. As a result, the recesses 2141 of the resin film sheet 214 tear at the sections 236 of the resin film sheet 214 that have been stretched, such that the torn sections of the resin film sheet 214 widen, forming openings at the sections where the resin film sheet 214 has torn.

The resin film sheet 214 is not significantly stretched at the sections 237,238 where the gear teeth 233 of the upper roll 231 and the gear teeth 235 of the lower roll 232 are not meshed. Consequently, even when the resin film sheet 241 passes through the stretching gear roll 230, the recesses 2141 formed in the recess-forming step are not torn and do not become openings at the sections 237,238 of the resin film sheet 214 where the gear teeth 233 of the upper roll 231 and the gear teeth 235 of the lower roll 232 are not meshed.

In the regions of the resin film sheet 214 where no recesses 2141 have been formed, the resin film sheet 214 is not torn even when the resin film sheet 214 is stretched to a high degree, at the section 236 where the gear teeth 233 of the upper roll 231 and the gear teeth 235 of the lower roll 232 are meshed. Consequently, openings are not formed in the regions of the resin film sheet 214 corresponding to the regions 14 on the outer sides of both edges 41 of the body section 10 in the widthwise direction of the absorbent body 4, and to the wing sections 5.

The absorbent article 1 according to an embodiment of the invention may also be modified as follows.

(1) The absorbent article may lack wing sections. That is, the absorbent article may consist of only the body section. In this case, pressure-sensitive adhesive sections are provided on the clothing side surface of the body section, allowing the absorbent article to be anchored to underwear even without wing sections.

(2) As long as it is possible to form in the absorbent article, at least on the outer sides of both edges in the widthwise direction of the absorbent body, the plurality of first fluid channels extending in the lengthwise direction and aligned in the widthwise direction, for flow of body fluid that has exuded from the absorbent body, and the plurality of second fluid channels connecting the adjacent first fluid channels, the first fluid channels and second fluid channels are not limited to fluid channels formed by the first protrusions of the top sheet and the back sheet and fluid channels formed by the second protrusions of the top sheet and the back sheet. For example, a resin layer may be formed by a method such as printing in the regions on the outer sides of both edges of the body section in the widthwise direction of the absorbent body, between the top sheet and the back sheet, at sections other than those corresponding to the fluid channels. In this case, the sections where the resin layer has not been formed between the top sheet and the back sheet become hollow, and therefore those sections can be used as fluid channels for inflow of body fluid that has exuded from the absorbent body.

(3) The first fluid channels 21 and second fluid channels 22 may be formed in the top sheet 2 between the bases 51 of the wing sections, which are on the outer sides of the edges 41 in the widthwise direction of the absorbent body 4 and constitute the borders between the body section 10 and the wing sections 5, and both edges 41 in the widthwise direction of the absorbent body 4, without forming first fluid channels and second fluid channels in the top sheet 2 at the wing sections 5. In this case as well it is possible to prevent body fluid that has exuded from the absorbent body 4 from leaking from the widthwise direction of the absorbent article 1 by pressure applied to the absorbent article 1.

Figure 13:
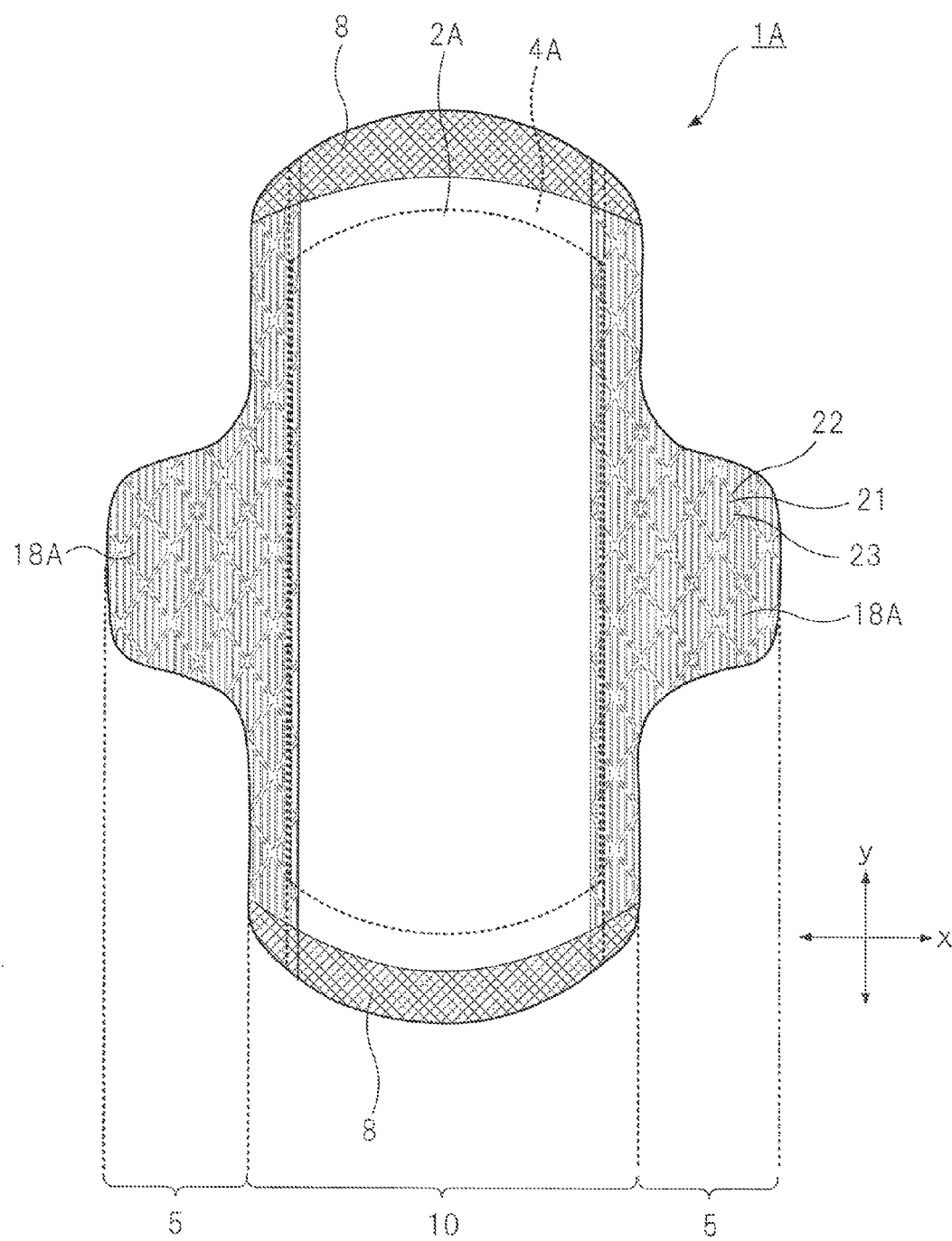
FIG. 13 is a plan view of a modified example of an embodiment of the absorbent article of the invention.

(4) When side sheets 18A are provided on both sides of the top sheet 2 in the widthwise direction, as in the absorbent article 1A illustrated in FIG. 13, the first protrusions 21, second protrusions 22 and bottom sections 23 may be formed on the side sheets 18A, at least on the outer sides of both edges in the widthwise direction of the absorbent body, and the bottom sections 23 of the side sheets 18A bonded with the back sheet. In this case, the plurality of first fluid channels extending in the lengthwise direction and aligned in the widthwise direction, for inflow of body fluid that has exuded from the absorbent body 4A, are formed by the first protrusions 21 of the side sheets 18A and the back sheet, while the plurality of second fluid channels that connect the adjacent first fluid channels are formed by the second protrusions 22 of the side sheets 18A and the back sheet. In this case as well, it is possible to prevent body fluid that has exuded from the absorbent body 4 from leaking from the widthwise direction of the absorbent article 1 under pressure applied to the absorbent article 1.

The top sheet 2A may be a nonwoven fabric in this case. Even when the top sheet 2A is a nonwoven fabric, it is still easy to fold the wing sections of the absorbent article along the shape of the edges of the leg openings of underwear.

The nonwoven fabric used for the top sheet 2A may be made of natural fibers or chemical fibers. Natural fibers to be used for the top sheet 2A include cellulose such as ground pulp and cotton. Chemical fibers to be used for the top sheet 2A include regenerated cellulose such as rayon and fibril rayon, semi-synthetic cellulose such as acetate and triacetate, thermoplastic hydrophobic chemical fibers, and hydrophilicized thermoplastic hydrophobic chemical fibers. Thermoplastic hydrophobic chemical fibers to be used for the top sheet 2A include monofilaments of polyethylene (PE), polypropylene (PP) and polyethylene terephthalate (PET), fibers obtained by graft polymerization of polyethylene and polypropylene, and composite fibers with a core-sheath structure or the like.

Incidentally, first protrusions, second protrusions and bottom sections may be provided in the top sheet 2A even when side sheets 18A are provided on both sides of the top sheet 2 in the widthwise direction.

That is, as long as the first protrusions, second protrusions and bottom sections are formed on the top sheet or side sheet at least on the outer sides of both edges in the widthwise direction of the absorbent body, the first protrusions, second protrusions and bottom sections may either be formed or not formed in the region of the top sheet in which the absorbent body is provided.

Figure 14:
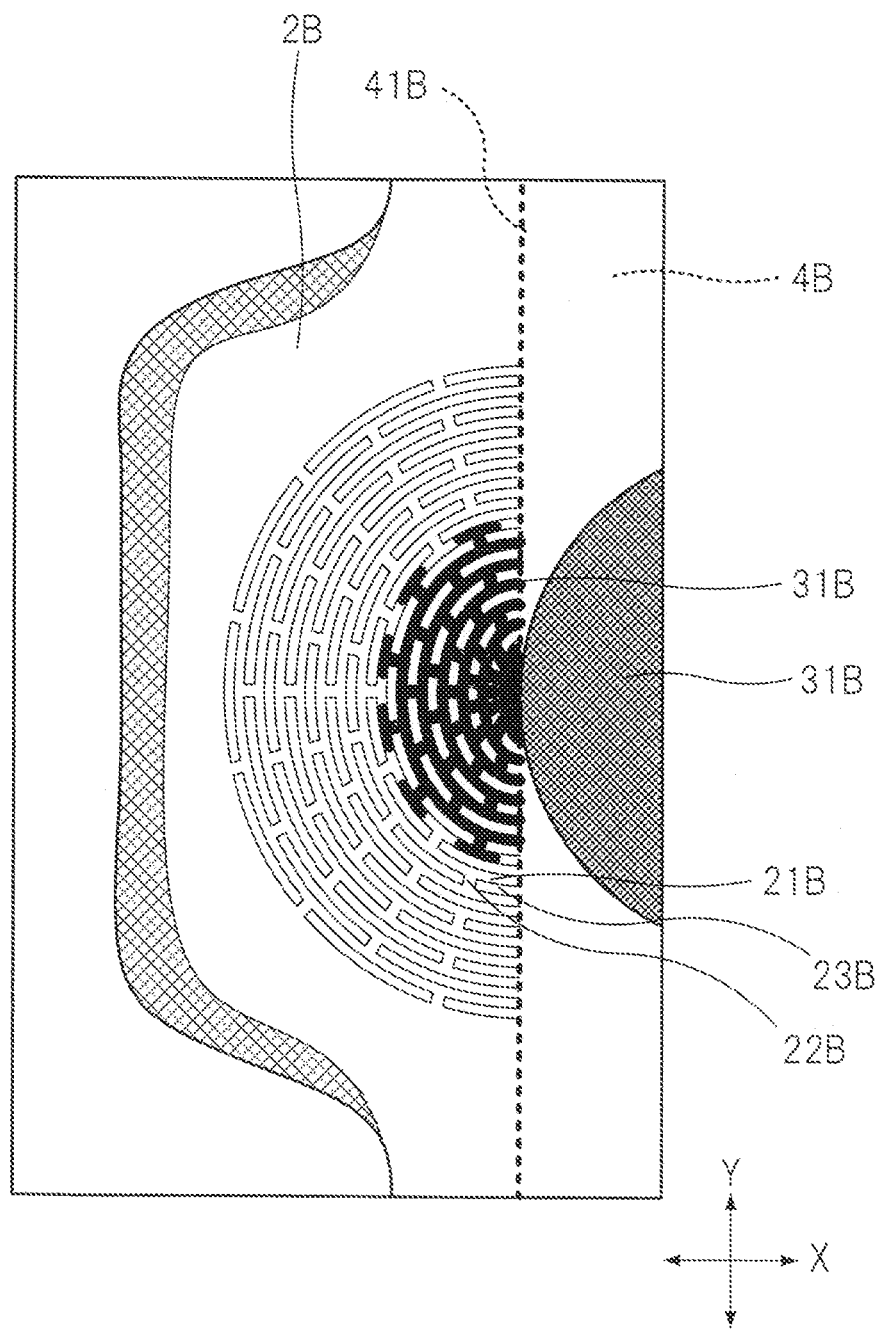
FIG. 14 is a plan view showing a region on the outer side of the edge in the widthwise direction of the absorbent body according to a modified example of an embodiment of the absorbent article of the invention.

(5) The first protrusions 21B of the top sheet 2B may be curved to protrude outward in the widthwise direction, at least on the outer sides of both edges 41B in the widthwise direction of the absorbent body 4B, as shown in FIG. 14. This will allow body fluid 31B that has exuded from the absorbent body 4B, and is flowing in the lengthwise direction (Y direction) through the fluid channels formed by the first protrusions 21B and the back sheet, to be re-absorbed into the absorbent body 4B. It will also be possible to further prevent body fluid 31B that has exuded from the absorbent body 4B from leaking from the widthwise direction of the absorbent article by pressure applied to the absorbent article. In addition, even if the edges 41B in the widthwise direction of the absorbent body 4B are not curved to protrude inward in the widthwise direction (X direction), body fluid 31B that has been exuded from the absorbent body 4B, and is flowing in the lengthwise direction (Y direction) through the fluid channels formed by the first protrusions 21B and the back sheet, will still be re-absorbed into the absorbent body 4B.

EXAMPLES

According to the invention, the blood modifying agent has a mechanism of lowering the viscosity and surface tension of blood, and therefore body fluid migrates by the blood modifying agent layer 24 to the absorbent body 4 without remaining in the top sheet 2, allowing it to be absorbed into the absorbent body 4. In the following examples, the blood modifying agent was confirmed to have a mechanism of lowering the viscosity and surface tension of blood. This was confirmed using a nonwoven fabric, which more readily retains body fluid than a resin film.

Example 1

Evaluation of Rewetting Rate and Absorbent Body Migration Rate

[Data of Blood Modifying Agents]

A commercially available sanitary napkin was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150-450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood modifying agents used for the experiment are listed below.

[($a_1$) Ester of a Chain Hydrocarbon Tetraol and at Least One Fatty Acid]

UNISTAR H-408BRS, product of NOF Corp.

Tetrapentaerythritol 2-ethylhexanoate, weight-average molecular weight: approximately 640

UNISTAR H-2408BRS-22, product of NOF Corp.

Mixture of tetrapentaerythritol 2-ethylhexanoate and di-neopentyl 2-ethylhexanoate glycol (58:42, mass ratio), weight-average molecular weight: approximately 520

[($a_2$) Ester of a Chain Hydrocarbon Triol and at Least One Fatty Acid]

Cetiol SB45DEO, Cognis Japan

Glycerin and fatty acid triester, with oleic acid or stearylic acid as the fatty acid.

SOY42, product of NOF Corp.

Glycerin and fatty acid triester with $C_{14}$ fatty acid:$C_{16}$ fatty acid:$C_{18}$ fatty acid:$C_{20}$ fatty acid (including both saturated fatty acids and unsaturated fatty acids) at a mass ratio of about 0.2:11:88:0.8, weight-average molecular weight: 880

Tri-C2L oil fatty acid glyceride, product of NOF Corp.

Glycerin and fatty acid triester with $C_8$ fatty acid:$C_{10}$ fatty acid:$C_{12}$ fatty acid at a mass ratio of about 37:7:56, weight-average molecular weight: approximately 570

Tri-CL oil fatty acid glyceride, product of NOF Corp.

Glycerin and fatty acid triester with $C_8$ fatty acid:$C_{12}$ fatty acid at a mass ratio of about 44:56, weight-average molecular weight: approximately 570

PANACET 810s, product of NOF Corp.

Glycerin and fatty acid triester with $C_8$ fatty acid:$C_{10}$ fatty acid at a mass ratio of about 85:15, weight-average molecular weight: approximately 480

PANACET 800, product of NOF Corp.

Glycerin and fatty acid triester with octanoic acid ($C_8$) as the entire fatty acid portion, weight-average molecular weight: approximately 470

PANACET 800B, product of NOF Corp.

Glycerin and fatty acid triester with 2-ethylhexanoic acid ($C_8$) as the entire fatty acid portion, weight-average molecular weight: approximately 470

NA36, product of NOF Corp.

Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880

Tri-coconut fatty acid glyceride, product of NOF Corp.

Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670

Caprylic acid diglyceride, product of NOF Corp.

Glycerin and fatty acid diester with octanoic acid as the fatty acid, weight-average molecular weight: approximately 340

[($a_3$) Ester of a Chain Hydrocarbon Diol and at Least One Fatty Acid]

COMPOL BL, product of NOF Corp.

Dodecanoic acid ($C_{12}$) monoester of butylene glycol, weight-average molecular weight: approximately 270

COMPOL BS, product of NOF Corp.

Octadecanoic acid ($C_{18}$) monoester of butylene glycol, weight-average molecular weight: approximately 350

UNISTAR H-208BRS, product of NOF Corp.

Neopentylglycol di-2-ethylhexanoate, weight-average molecular weight: approximately 360.

[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]

Tributyl O-acetylcitrate, product of Tokyo Kasei Kogyo Co., Ltd.

Weight-average molecular weight: approximately 400

[($c_3$) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]

Dioctyl adipate, product of Wako Pure Chemical Industries, Ltd.

Weight-average molecular weight: approximately 380

[($d_3$) Ester of a Fatty Acid and an Aliphatic Monohydric Alcohol]

ELECTOL WE20, product of NOF Corp.

Ester of dodecanoic acid ($C_{12}$) and dodecyl alcohol ($C_{12}$), weight-average molecular weight: approximately 360

ELECTOL WE40, product of NOF Corp.

Ester of tetradecanoic acid ($C_{14}$) and dodecyl alcohol ($C_{12}$), weight-average molecular weight: approximately 390

[($e_1$) Polyoxy $C_2$-$C_6$ Alkylene Glycol]

UNIOL D-1000, product of NOF Corp.

Polypropylene glycol, weight-average molecular weight: approximately 1,000

UNIOL D-1200, product of NOF Corp.

Polypropylene glycol, weight-average molecular weight: approximately 1,160

UNIOL D-3000, product of NOF Corp.

Polypropylene glycol, weight-average molecular weight: approximately 3,000

UNIOL D-4000, product of NOF Corp.

Polypropylene glycol, weight-average molecular weight: approximately 4,000

UNIOL PB500, product of NOF Corp.

Polybutylene glycol, weight-average molecular weight: approximately 500

UNIOL PB700, product of NOF Corp.

Polyoxybutylenepolyoxypropylene glycol, weight-average molecular weight: approximately 700

UNIOL PB1000R, product of NOF Corp.

Polybutylene glycol, weight-average molecular weight: approximately 1,000

[($e_2$) Ester of a Polyoxy $C_2$-$C_6$ Alkylene Glycol and at Least One Fatty Acid]

WILBRITE cp9, product of NOF Corp.

Polybutylene glycol compound with OH groups at both ends esterified by hexadecanoic acid ($C_{16}$), weight-average molecular weight: approximately 1,150

[($e_3$) Ether of Polyoxy $C_2$-$C_6$ Alkylene Glycol and at Least One Fatty Acid]

UNILUBE MS-70K, product of NOF Corp.

Stearyl ether of polypropylene glycol, approximately 15 repeating units, weight-average molecular weight: approximately 1,140

[($e_5$) Ether of a Polyoxy $C_2$-$C_6$ Alkylene Glycol with Chain Hydrocarbon Tetraol, Chain Hydrocarbon Triol or Chain Hydrocarbon Diol]

UNILUBE 5TP-300 KB

Polyoxyethylenepolyoxypropylene pentaerythritol ether, produced by addition of 5 mol of ethylene oxide and 65 mol of propylene oxide to 1 mol of pentaerythritol, weight-average molecular weight: 4,130

UNIOL TG-3000, product of NOF Corp.

Glyceryl ether of polypropylene glycol, approximately 16 repeating units, weight-average molecular weight: approximately 3,000

UNIOL TG-4000, product of NOF Corp.

Glyceryl ether of polypropylene glycol, approximately 16 repeating units, weight-average molecular weight: approximately 4,000

[($f_1$) Chain Alkane]

PARLEAM 6, product of NOF Corp.

Branched hydrocarbon, produced by copolymerization of liquid isoparaffin, isobutene and n-butene followed by hydrogen addition, polymerization degree: approximately 5-10, weight-average molecular weight: approximately 330

[Other Components]

NA50, product of NOF Corp.

Glycerin and fatty acid triester obtained by addition of hydrogen to NA36 for reduced proportion of double bonds from unsaturated fatty acid starting material, weight-average molecular weight: approximately 880

(Caprylic acid/capric acid) monoglyceride, product of NOF Corp.

Glycerin and fatty acid monoester, with octanoic acid ($C_8$) and decanoic acid ($C_{10}$) at a mass ratio of about 85:15, weight-average molecular weight: approximately 220

Monomuls 90-L2 lauric acid monoglyceride, product of Cognis Japan

Isopropyl citrate, product of Tokyo Kasei Kogyo Co., Ltd.

Weight-average molecular weight: approximately 230

Diisostearyl malate

Weight-average molecular weight: approximately 640

UNIOL D-400, product of NOF Corp.

Polypropylene glycol, weight-average molecular weight: approximately 400

PEG1500, product of NOF Corp.

Polyethylene glycol, weight-average molecular weight: approximately 1,500-1,600

NONION S-6, product of NOF Corp.

Polyoxyethylene monostearate, approximately 7 repeating units, weight-average molecular weight: approximately 880

WILBRITE s753, product of NOF Corp.

Polyoxyethylenepolyoxypropylene polyoxybutylene glycerin, weight-average molecular weight: approximately 960

UNIOL TG-330, product of NOF Corp.

Glyceryl ether of polypropylene glycol, approximately 6 repeating units, weight-average molecular weight: approximately 330

UNIOL TG-1000, product of NOF Corp.

Glyceryl ether of polypropylene glycol, approximately 16 repeating units, weight-average molecular weight: approximately 1,000

UNILUBE DGP-700, product of NOF Corp.

Diglyceryl ether of polypropylene glycol, approximately 9 repeating units, weight-average molecular weight: approximately 700

UNIOX HC60, product of NOF Corp.

Polyoxyethylene hydrogenated castor oil, weight-average molecular weight: approximately 3,570

Vaseline, product of Cognis Japan

Petroleum-derived hydrocarbon, semi-solid

The IOBs, melting points and water solubilities of the samples are shown in Table 2.

The water solubility was measured by the method described above, and samples that dissolved 24 hours after addition of 20.0 g to 100 g of desalted water were evaluated as "20 g<", and samples of which 0.05 g dissolved in 100 g of desalted water but 1.00 g did not dissolve were evaluated as 0.05-1.00 g.

For the melting point, "<45" indicates a melting point of below 45° C.

The skin contact surface of the top sheet of the sanitary napkin was coated with the aforementioned blood modifying agent. Each blood modifying agent was used directly, when the blood modifying agent was liquid at room temperature, or when the blood modifying agent was solid at room temperature it was heated to its melting point of +20° C., and a control seam HMA gun was used for atomization of the blood modifying agent and coating onto the entire skin contact surface of the top sheet to a basis weight of about 5 g/m².

Figure 15:
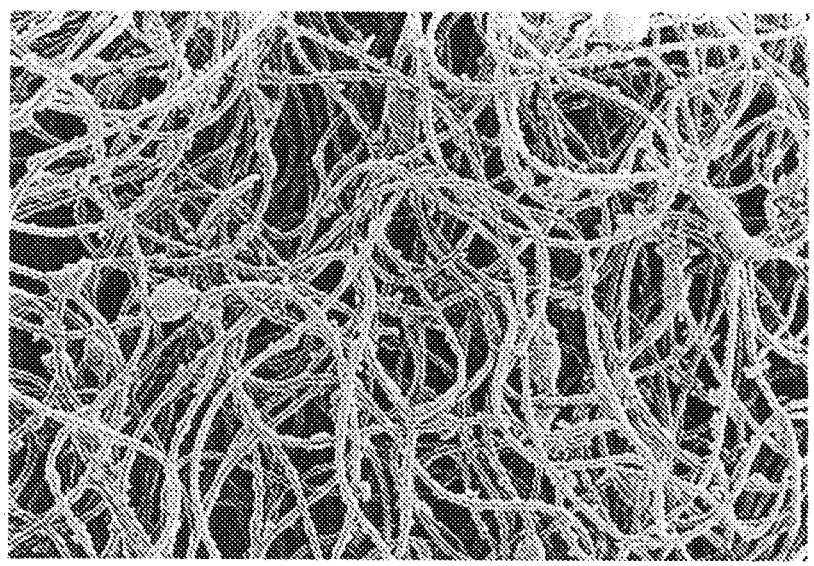
FIG. 15 is an electron micrograph of the skin contact surface of a top sheet in a sanitary napkin wherein the top sheet comprises tri-C2L oil fatty acid glycerides.

FIG. 15 is an electron micrograph of the skin contact surface of a top sheet in a sanitary napkin (No. 2-5) wherein the top sheet comprises tri-C2L oil fatty acid glycerides. As clearly seen in FIG. 15, the tri-C2L oil fatty acid glycerides are present on the fiber surfaces as fine particulates.

In accordance with the above procedures, the rewetting rate and absorber migration rate were measured. The results are shown below in Table 2.

[Test Methods]

An acrylic board with an opened hole (200 mm×100 mm, 125 g, with a 40 mm×10 mm hole opened at the center) was placed on a top sheet comprising each blood modifying agent, and 3 g of horse EDTA blood at 37±1° C. (obtained by adding appropriate amount of ethylenediaminetetraacetic acid (hereunder, "EDTA") to horse blood to prevent coagulation) was dropped through the hole using a pipette (once), and after 1 minute, 3 g of horse EDTA blood at 37±1° C. was again added dropwise through the acrylic board hole with a pipette (twice).

After the second dropping of blood, the acrylic board was immediately removed and 10 sheets of filter paper (Advantec Toyo Kaisha, Ltd, Qualitative Filter Paper No. 2, 50 mm×35 mm) were placed on the location where the blood had been dropped, and then a weight was placed thereover to a pressure of 30 g/cm². After 1 minute, the filter paper was removed and the "rewetting rate" was calculated by the following formula.

Rewetting rate (%)=100×(filter paper mass after test−initial filter paper mass)/6

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 2.

Then the whiteness of the skin contact surface of the top sheet after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining.

The results are summarized below in Table 2.

TABLE 2

| | | Blood modifying agent | | Melting | Water solubility | Weight-average | Rewetting | Absorber migration | Top sheet |
|---|---|---|---|---|---|---|---|---|---|
| No. | Type | Product name | IOB | point (° C.) | (g) | mol. wt. | rate (%) | rate (sec) | whiteness |
| 2-1 | (A₁) | UNISTAR H-408BRS | 0.13 | <−5 | <0.05 | 640 | 1.2 | 3 | VG |
| 2-2 | | UNISTAR H-2408BRS-22 | 0.18 | <−5 | <0.05 | 520 | 2.0 | 3 | VG |
| 2-3 | (A₂) | CETIOL SB45DEO | 0.16 | 44 | <0.05 | | 7.0 | 6 | VG |
| 2-4 | | SOY42 | 0.16 | 43 | <0.05 | 880 | 5.8 | 8 | VG |
| 2-5 | | Tri-C2L oil fatty acid glyceride | 0.27 | 37 | <0.05 | 570 | 0.3 | 3 | VG |
| 2-6 | | Tri-CL oil fatty acid glyceride | 0.28 | 38 | <0.05 | 570 | 1.7 | 3 | VG |
| 2-7 | | PANACET 810s | 0.32 | −5 | <0.05 | 480 | 2.8 | 3 | VG |
| 2-8 | | PANACET 800 | 0.33 | −5 | <0.05 | 470 | 0.3 | 3 | VG |
| 2-9 | | PANACET 800B | 0.33 | −5 | <0.05 | 470 | 2.0 | 3 | VG |
| 2-10 | | NA36 | 0.16 | 37 | <0.05 | 880 | 3.9 | 5 | VG |
| 2-11 | | Tri-coconut fatty acid glyceride | 0.28 | 30 | <0.05 | 670 | 4.3 | 5 | VG |
| 2-12 | | Caprylic acid diglyceride | 0.58 | <45 | <0.05 | 340 | 4.2 | 9 | G |
| 2-13 | (A₃) | COMPOL BL | 0.50 | 2 | <0.05 | 270 | 2.0 | 5 | G |
| 2-14 | | COMPOL BS | 0.36 | 37 | <0.05 | 350 | 7.9 | 9 | G |
| 2-15 | | UNISTAR H-208BRS | 0.24 | <−5 | <0.05 | 360 | 2.0 | 5 | VG |
| 2-16 | (C₂) | Tributyl O-acetylcitrate | 0.60 | <45 | <0.05 | 400 | 6.2 | 8 | VG |
| 2-17 | (C₃) | Dioctyl adipate | 0.27 | <45 | <0.05 | 380 | 1.7 | 6 | VG |
| 2-18 | (D₃) | ELECTOL WE20 | 0.13 | 29 | <0.05 | 360 | 1.8 | 5 | VG |
| 2-19 | | ELECTOL WE40 | 0.12 | 37 | <0.05 | 390 | 1.8 | 4 | VG |
| 2-20 | (E₁) | UNIOL D-1000 | 0.51 | <45 | <0.05 | 1,000 | 6.8 | 15 | F |
| 2-21 | | UNIOL D-1200 | 0.48 | <45 | <0.05 | 1,160 | 0.5 | 11 | F |
| 2-22 | | UNIOL D-3000 | 0.39 | <45 | <0.05 | 3,000 | 1.7 | 10 | |
| 2-23 | | UNIOL D-4000 | 0.38 | <45 | <0.05 | 4,000 | 1.0 | 7 | G |
| 2-24 | (E₁) | UNIOL PB500 | 0.44 | <45 | <0.05 | 500 | 4.5 | 4 | G |
| 2-25 | | UNIOL PB700 | 0.49 | −5 | <0.05 | 700 | 2.8 | 5 | G |
| 2-26 | | UNIOL PB1000R | 0.40 | <45 | <0.05 | 1,000 | 4.0 | 4 | G |
| 2-27 | (E₂) | WILBRITE cp9 | 0.21 | 35 | <0.05 | 1,150 | 1.4 | 3 | G |
| 2-28 | (E₃) | UNILUBE MS-70K | 0.30 | <−10 | <0.05 | 1,140 | 6.7 | 3 | G |
| 2-29 | (E₅) | UNILUBE 5TP-300KB | 0.39 | <45 | <0.05 | 4,130 | 2.0 | 6 | G |
| 2-30 | | UNIOL TG-3000 | 0.42 | <45 | <0.05 | 3,000 | 0.8 | 6 | G |
| 2-31 | | UNIOL TG-4000 | 0.40 | <45 | <0.05 | 4,000 | 2.0 | 6 | G |
| 2-32 | (F₁) | PARLEAM 6 | 0.00 | −5 | <0.05 | 330 | 6.0 | 8 | VG |
| 2-33 | | NA50 | 0.18 | 52 | <0.05 | 880 | 15.5 | 60 | P |
| 2-34 | | (Caprylic acid/capric acid) monoglyceride | 1.15 | <45 | 20< | 220 | 4.0 | 4 | P |

TABLE 2-continued

| | Blood modifying agent | | | Melting | Water solubility | Weight-average | Rewetting | Absorber migration | Top sheet |
|---|---|---|---|---|---|---|---|---|---|
| No. | Type | Product name | IOB | point (° C.) | (g) | mol. wt. | rate (%) | rate (sec) | whiteness |
| 2-35 | | Monomuls 90-L2 lauric acid monoglyceride | 0.87 | 58 | 20< | | 6.2 | 7 | P |
| 2-36 | | Isopropyl citrate | 1.56 | <45 | 20< | 230 | 12.2 | 5 | G |
| 2-37 | | Diisostearyl malate | 0.28 | <45 | 20< | 640 | 5.5 | 8 | F |
| 2-38 | | UNIOL D-400 | 0.76 | <45 | 0.05< | 400 | 8.7 | 40 | P |
| 2-39 | | PEG1500 | 0.78 | 40 | 20< | 1,500-1,600 | 11.0 | 38 | P |
| 2-40 | | NONION S-6 | 0.44 | 37 | 0.05< | 880 | 8.4 | 7 | P |
| 2-41 | | WILBRITE s753 | 0.67 | −5 | 20< | 960 | 9.3 | 9 | F |
| 2-42 | | UNIOL TG-330 | 1.27 | <45 | 0.05< | 330 | — | — | — |
| 2-43 | | UNIOL TG-1000 | 0.61 | <45 | <0.05 | 1,000 | 14.2 | 7 | G |
| 2-44 | | UNILUBE DGP-700 | 0.91 | <0 | 0.05< | 700 | 8.0 | 10 | F |
| 2-45 | | UNIOX HC60 | 0.46 | 33 | 0.05-1.00 | 3,570 | 14.6 | 46 | P |
| 2-46 | | Vaseline | 0.00 | 55 | <0.05 | | 9.7 | 10 | F |
| 2-47 | | None | — | — | — | — | 22.7 | 60< | P |

In the absence of a blood modifying agent, the rewetting rate was 22.7% and the absorbent body migration rate was greater than 60 seconds, but the glycerin and fatty acid triesters all produced rewetting rates of no greater than 7.0% and absorbent body migration rates of no longer than 8 seconds, and therefore significantly improved the absorption performance. Of the glycerin and fatty acid triesters, however, no great improvement in absorption performance was seen with NA50 which had a melting point of above 45° C.

Similarly, the absorption performance was also significantly improved with blood modifying agents having an IOB of about 0.00-0.60, a melting point of no higher than about 45° C. and a water solubility of no greater than about 0.05 g in 100 g of water at 25° C. Rewetting rates of no greater than 7.9% and absorbent body migration rates of no longer than 15 seconds were achieved.

Next, several volunteer subjects were asked to wear sanitary napkins Nos. (2-1)-(2-47), and the obtained responses indicated that with the sanitary napkins comprising blood modifying agents Nos. (2-1)-(2-32), the top sheets had no sticky feel and the top sheets were smooth, even after absorption of menstrual blood.

Also, with sanitary napkins Nos. (2-1)-(2-32), and particularly with sanitary napkins that comprised blood modifying agents Nos. (2-1)-(2-11), (2-15)-(2-19) and (2-32), the skin contact surfaces of the top sheets after absorption of menstrual blood had not been reddened by the blood and the unpleasantness was minimal.

Example 2

The rewetting rate was evaluated for blood from different animals in accordance with the above procedures. The following blood was used for the test.

[Animal Species]
 (1) Human
 (2) Horse
 (3) Sheep

[Types of Blood]
 Defibrinated blood: blood sampled and agitated together with glass beads in an Erlenmeyer flask for approximately 5 minutes.
 EDTA blood: 65 mL of venous blood with addition of 0.5 mL of a 12% EDTA·2K isotonic sodium chloride solution.

[Fractionation]
 Serum or blood plasma: Supernatant obtained after centrifugation of defibrinated blood or EDTA blood for 10 minutes at room temperature at about 1900 G.
 Blood cells: Obtained by removing the serum from the blood, washing twice with phosphate buffered saline (PBS), and adding phosphate buffered saline to the removed serum portion.

An absorbent article was produced in the same manner as Example 2, except that the tri-C2L oil fatty acid glyceride was coated at a basis weight of about 5 g/m², and the rewetting rate of each of the aforementioned blood samples was evaluated. Measurement was performed 3 times for each blood sample, and the average value was recorded.

The results are shown in Table 3 below.

TABLE 3

| | | | Rewetting rate (%) | |
|---|---|---|---|---|
| No. | Animal species | Type of blood | With blood modifying agent | Without blood modifying agent |
| 1 | Human | Defibrinated blood | 1.6 | 5.0 |
| 2 | | Defibrinated serum | 0.2 | 2.6 |
| 3 | | Defibrinated blood cells | 0.2 | 1.8 |
| 4 | | EDTA blood | 2.6 | 10.4 |
| 5 | | EDTA plasma | 0.0 | 5.8 |
| 6 | | EDTA blood cells | 0.2 | 4.3 |
| 7 | Horse | Defibrinated blood | 0.0 | 8.6 |
| 8 | | Defibrinated serum | 0.2 | 4.2 |
| 9 | | Defibrinated blood cells | 0.2 | 1.0 |
| 10 | | EDTA blood | 6.0 | 15.7 |
| 11 | | EDTA plasma | 0.1 | 9.0 |
| 12 | | EDTA blood cells | 0.1 | 1.8 |
| 13 | Sheep | Defibrinated blood | 0.2 | 5.4 |
| 14 | | Defibrinated serum | 0.3 | 1.2 |
| 15 | | Defibrinated blood cells | 0.1 | 1.1 |
| 16 | | EDTA blood | 2.9 | 8.9 |
| 17 | | EDTA plasma | 0.0 | 4.9 |
| 18 | | EDTA blood cells | 0.2 | 1.6 |

The same trend was seen with human and sheep blood as with the horse EDTA blood, as obtained in Example 2. A similar trend was also observed with defibrinated blood and EDTA blood.

Example 3

Evaluation of Blood Retention

The blood retention was evaluated for a top sheet comprising a blood modifying agent and a top sheet comprising no blood modifying agent.

[Test Methods]

(1) A tri-C2L oil fatty acid glyceride was atomized on the skin contact surface of a top sheet formed from an air-through nonwoven fabric (composite fiber composed of polyester and polyethylene terephthalate, basis weight: 35 g/m$^2$), using a control seam HMA gun, for coating to a basis weight of about 5 g/m$^2$. For comparison, there was also prepared a sheet without coating with the tri-C2L oil fatty acid glyceride. Next, both the tri-C2L oil fatty acid glyceride-coated top sheet and the non-coated top sheet were cut to a size of 0.2 g, and the mass (a) of the cell strainer+top sheet was precisely measured.

(2) After adding about 2 mL of horse EDTA blood from the skin contact surface side, it was allowed to stand for 1 minute.

(3) The cell strainer was set in a centrifuge tube, and subjected to spin-down to remove the excess horse EDTA blood.

(4) The mass (b) of the top sheet containing the cell strainer+horse EDTA blood was measured.

(5) The initial absorption (g) per 1 g of top sheet was calculated by the following formula.

Initial absorption=[mass (b)−mass (a)]/0.2

(6) The cell strainer was again set in the centrifuge tube and centrifuged at room temperature for 1 minute at approximately 1,200 G.

(7) The mass (c) of the top sheet containing the cell strainer+horse EDTA blood was measured.

(8) The post-test absorption (g) per 1 g of top sheet was calculated by the following formula.

Post-test absorption=[mass (c)−mass (a)]/0.2

(9) The blood retention (%) was calculated according to the following formula.

Blood retention (%)=100×post-test absorption/initial absorption

The measurement was conducted 3 times, and the average value was recorded.

The results are shown in Table 4 below.

TABLE 4

| | Blood retention (%) | |
|---|---|---|
| | With blood modifying agent | Without blood modifying agent |
| Horse EDTA blood | 3.3 | 9.2 |

The top sheets comprising blood modifying agents had low blood retentions, suggesting that blood rapidly migrated into the absorbent body after absorption.

Example 4

Viscosity of Blood Containing Blood Modifying Agent

The viscosity of the blood modifying agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood modifying agent was 50.4 mPa·s. Thus, the horse defibrinated blood containing 2 mass % PANACET 810s clearly had an approximately 90% lower viscosity than the blood containing no blood modifying agent.

It is known that blood contains components such as blood cells and has thixotropy, and it has been found that the blood modifying agent of this disclosure can lower blood viscosity in the low viscosity range. Lowering the blood viscosity presumably allows absorbed menstrual blood to rapidly migrate from the top sheet to the absorbent body.

Example 5

Photomicrograph of Blood Modifying Agent-Containing Blood

Menstrual blood was sampled from healthy volunteers onto Saran wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood modifying agent is shown in FIG. 16(a), and a photomicrograph of menstrual blood containing PANACET 810s is shown in FIG. 16(b).

As shown FIG. 16, it is seen that the erythrocytes formed aggregates such as rouleaux in the menstrual blood containing no blood modifying agent, while the erythrocytes were stably dispersed in the menstrual blood containing PANACET 810s. This suggests that the blood modifying agent functions to stabilize erythrocytes in blood.

Example 6

Surface Tension of Blood Containing Blood Modifying Agent

The surface tension of blood containing a blood modifying agent was measured by the pendant drop method, using a Drop Master500 contact angle meter by Kyowa Interface Science Co., Ltd. The surface tension was measured after adding a prescribed amount of blood modifying agent to sheep defibrinated blood, and thoroughly shaking.

The measurement was accomplished automatically with a device, and the surface tension 7 was determined by the following formula (see FIG. 17).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 5, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 5 below.

TABLE 5

| | Blood modifying agent | | | |
|---|---|---|---|---|
| No. | Type | Amount (mass %) | Measuring temperature (° C.) | Surface tension (mN/m) |
| 1 | — | — | 35 | 62.1 |
| 2 | PANACET 810s | 0.01 | 35 | 61.5 |
| 3 | | 0.05 | 35 | 58.2 |
| 4 | | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Table 5 shows that the blood modifying agent can lower the surface tension of blood despite its very low solubility in water, as seen by a water solubility of about 0.00-about 0.05 g in 100 g of water at 25° C.

Lowering the surface tension of blood presumably allows absorbed blood to rapidly migrate from the top sheet to the absorbent body, without being retained between the top sheet fibers.

Any of the aforementioned embodiments may also be applied in combination with the modifications. The modifications may also be applied in combination with each other.

The explanation above is merely for illustration, and the invention is in no way restricted by the described embodiment.

EXPLANATION OF SYMBOLS 1, 1A Absorbent articles
2, 2A, 2B Top sheets
3 Back sheet
4, 4A, 4B Absorbent bodies
5 Wing section
6 Pressure-sensitive adhesive section
7 Compressed groove
8 Seal section
10 Body section
18A Side sheet
21, 21B First protrusions
22, 22B Second protrusions
23, 23B Bottom sections
24 Blood modifying agent layer
25 Opening
26 Side of first protrusion
31 Body fluid exuded from absorbent body
100 Top sheet production apparatus
120 Pattern drum
130 Embossing apparatus
140 Back sheet roll
150 Cutter
160 Modifying agent-coating sprayer
210 Resin film sheet roll
212, 214, 216 Resin film sheets
220 Recess-forming roll
230 Stretching gear roll
231 Upper roll
232 Lower roll
233, 235 Gear teeth
234 Interrupted location of gear teeth

What is claimed is:

1. An absorbent article having a lengthwise direction, a widthwise direction, a skin contact side and a non-skin contact clothing side, the absorbent article comprising a liquid-permeable top sheet provided on the skin side, a liquid-impermeable back sheet provided on the clothing side and a liquid-retaining absorbent body including edges extending in the lengthwise direction and opposed in the widthwise direction and provided between the top sheet and the back sheet, wherein the absorbent article includes, at least laterally outside of both absorbent body edges in the widthwise direction, a plurality of first fluid channels and a plurality of second fluid channels for inflow of body fluid that has exuded from the absorbent body, the plurality of first fluid channels extending in the lengthwise direction and being aligned in the widthwise direction, the plurality of second fluid channels connecting the adjacent first fluid channels, wherein the top sheet includes a plurality of first protrusions extending in the lengthwise direction and aligned in the widthwise direction, a plurality of second protrusions connecting the adjacent first protrusions, and bottom sections at sections that are to form bases of the first protrusions and the second protrusions, in at least a portion of a region in which the absorbent body is provided, the top sheet further includes a blood modifying agent layer provided on the skin side, in at least the portion of the region in which the absorbent body is provided, wherein each protrusion of the first protrusions comprises a first protruding side and a laterally opposed second protruding side, the first protrusions having a plurality of openings arranged in the lengthwise direction on first and second protruding sides, in at least the portion of the region in which the absorbent body is provided, and wherein the blood modifying agent of the blood modifying agent layer has an IOB of 0.00 to 0.60, a melting point of no higher than 45° C. and a water solubility of no greater than 0.05 g in 100 g of water at 25° C.

2. The absorbent article according to claim 1, wherein the top sheet includes, at least laterally outside of both of the absorbent body edges in the widthwise direction, the plurality of first protrusions, the plurality of second protrusions, and the bottom sections, the bottom sections of the top sheet are bonded to the back sheet at least laterally outside of both of the absorbent body edges in the widthwise direction, the first fluid channels are composed of the first protrusions of the top sheet, and the back sheet, and the second fluid channels are composed of the second protrusions of the top sheet, and the back sheet.

3. The absorbent article according to claim 1, which further comprises a pair of side sheets on sides of the topsheet in the widthwise direction, the pair of the side sheets are provided at least laterally outside of both of the absorbent body edges in the widthwise direction, the pair of the side sheets include, at least laterally outside of both of the absorbent body edges in the widthwise direction, the plurality of first protrusions, the plurality of second protrusions, and the bottom sections, the bottom sections of the side sheets are bonded to the back sheet, the first fluid channels are composed of the first protrusions of the side sheets, and the back sheet, and the second fluid channels are composed of the second protrusions of the side sheets, and the back sheet.

4. The absorbent article according to claim 1, wherein the absorbent body edges in the widthwise direction are curved so as to protrude inward in the widthwise direction.

5. The absorbent article according to claim 1, wherein the first fluid channels are curved so as to protrude outward in the widthwise direction, at least laterally outside of both of the absorbent body edges in the widthwise direction.

6. The absorbent article according to claim 1, which comprises a body section with the top sheet, the back sheet and the absorbent body, and a pair of wing sections provided on sides of the body section, extending in the widthwise direction from both sides of the body section.

7. The absorbent article according to claim 1, which comprises seal sections that seal lengthwise ends of the first fluid channels.

8. The absorbent article according to claim 1, wherein the blood modifying agent is selected from the group consisting of the following items (i)-(iii), and any combination thereof:
a hydrocarbon;
(ii) a compound having (ii-1) a hydrocarbon moiety, and (ii-2) one or more groups each selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more groups each selected from the group consisting of carbonyl group (—CO—) and oxy group (—O—) inserted between a C—C single bond of the hydrocarbon moiety, and (iii-3) one or more groups each selected from the group consisting of carboxyl group (—COOH) and hydroxyl group (—OH) substituting a hydrogen of the hydrocarbon moiety;
wherein when 2 or more oxy groups are inserted in the compound of (ii) or (iii), the oxy groups are not adjacent.

9. The absorbent article according to claim 1, wherein the blood modifying agent is selected from the group consisting of the following items (i')-(iii'), and any combination thereof:
(i') a hydrocarbon;
(ii') a compound having at least (ii'-1) a hydrocarbon moiety, and (ii'-2) one or more bonds each selected from the group consisting of carbonyl bond (—CO—), at least one ester bond (—COO—), at least one carbonate bond (—OCOO—), and at least one ether bond (—O—) inserted between a C—C single bond of the hydrocarbon moiety; and
(iii') a compound having at least (iii'-1) a hydrocarbon moiety, (iii'-2) one or more bonds each selected from the group consisting of carbonyl bond (—CO—), at least one ester bond (—COO—), at least one carbonate bond (—OCOO—), and at least one ether bond (—O—) inserted between a C—C single bond of a hydrocarbon moiety, and (iii'-3) one or more groups each selected from the group consisting of carboxyl group (—COOH) and hydroxyl group (—OH) substituting a hydrogen on the hydrocarbon moiety;
wherein when 2 or more same or different bonds are inserted in the compound of (ii') or (iii'), the bonds are not adjacent.

10. The absorbent article according to claim 1, wherein the blood modifying agent is selected from the group consisting of the following items (A)-(F), and any combination thereof:
(A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;
(B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;
(C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;
(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety;
(E) a polyoxy $C_2$-$C_6$ alkylene glycol, or alkyl ester or alkyl ether thereof; and
(F) a chain hydrocarbon.

11. The absorbent article according to claim 1, wherein the blood modifying agent is selected from the group consisting of ($a_1$) esters of chain hydrocarbon tetraols and at least one fatty acid, ($a_2$) esters of chain hydrocarbon triols and at least one fatty acid, ($a_3$) esters of chain hydrocarbon diols and at least one fatty acid, ($b_1$) ethers of chain hydrocarbon tetraols and at least one aliphatic monohydric alcohol, ($b_2$) ethers of chain hydrocarbon triols and at least one aliphatic monohydric alcohol, ($b_3$) ethers of chain hydrocarbon diols and at least one aliphatic monohydric alcohol, ($c_1$) esters of chain hydrocarbon tetracarboxylic acids, hydroxy acids, alkoxy acids or oxoacids with 4 carboxyl groups, and at least one aliphatic monohydric alcohol, ($c_2$) esters of chain hydrocarbon tricarboxylic acids, hydroxy acids, alkoxy acids or oxoacids with 3 carboxyl groups, and at least one aliphatic monohydric alcohol, ($c_3$) esters of chain hydrocarbon dicarboxylic acids, hydroxy acids, alkoxy acids or oxoacids with 2 carboxyl groups, and at least one aliphatic monohydric alcohol, ($d_1$) ethers of aliphatic monohydric alcohols and aliphatic monohydric alcohols, ($d_2$) dialkyl ketones, ($d_3$) esters of fatty acids and aliphatic monohydric alcohols, ($d_4$) dialkyl carbonates, ($e_1$) polyoxy $C_2$-$C_6$ alkylene glycols, ($e_2$) esters of polyoxy $C_2$-$C_6$ alkylene glycols and at least one fatty acid, ($e_3$) ethers of polyoxy $C_2$-$C_6$ alkylene glycols and at least one aliphatic monohydric alcohol, ($e_4$) esters of polyoxy $C_2$-$C_6$ alkylene glycols with chain hydrocarbon tetracarboxylic acids, chain hydrocarbon tricarboxylic acids or chain hydrocarbon dicarboxylic acids, ($e_5$) ethers of polyoxy $C_2$-$C_6$ alkylene glycols with chain hydrocarbon tetraols, chain hydrocarbon triols or chain hydrocarbon diols, and ($f_1$) chain alkanes.

* * * * *